US006485969B1

(12) United States Patent
Asem et al.

(10) Patent No.: US 6,485,969 B1
(45) Date of Patent: Nov. 26, 2002

(54) BIOMATERIAL DERIVED FROM FOLLICLE BASEMENT MEMBRANES

(75) Inventors: Elikplimi K. Asem, West Lafayette, IN (US); John J. Turek, West Lafayette, IN (US); J. Paul Robinson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/582,179
(22) PCT Filed: Dec. 22, 1998
(86) PCT No.: PCT/US98/27289
§ 371 (c)(1), (2), (4) Date: Jun. 22, 2000
(87) PCT Pub. No.: WO99/32607
PCT Pub. Date: Jul. 1, 1999

Related U.S. Application Data
(60) Provisional application No. 60/068,769, filed on Dec. 23, 1997.

(51) Int. Cl.[7] .................................................. C12N 5/00
(52) U.S. Cl. ........................ 435/325; 435/373; 435/378; 435/401; 435/1.1
(58) Field of Search ............................... 435/325, 373, 435/378, 401, 1.1

(56) References Cited

U.S. PATENT DOCUMENTS

| | | |
|---|---|---|
| 4,829,000 A | 5/1989 | Kleinman et al. |
| 4,902,508 A | 2/1990 | Badylak et al. |
| 4,921,808 A * | 5/1990 | Schneyer et al. |
| 5,275,826 A | 1/1994 | Badylak et al. |
| 5,281,422 A | 1/1994 | Badylak et al. |
| 5,352,463 A | 10/1994 | Badylak et al. |
| 5,821,121 A * | 10/1998 | Brothers |

FOREIGN PATENT DOCUMENTS

| EP | 0 218 065 A 2 | 4/1987 |
|---|---|---|

OTHER PUBLICATIONS

"Steroidogenesis and Actions in the Hen Ovary," by A.L. Johnson, Critical Reviews in Poultry Biology (1990) vol. 2(4), 319–346.

"Crude Liver Membrane Fractions as Substrate Preserve Liver–Specific Functions in Long–Term, Serum–Free Rat Hepatocyte Cultures," by B. Saad et al., In Vitro Cell Dev. Biol. (1993) vol. 29A, 32–40.

"Crude Liver Membrane Fractions and Extracellular Matrix Components as Substrata Regulate Differentially the Preservation and Inducibility of Cytochrome P–450 Isoenzymes in Cultured Rat Hepatocytes," by B. Saad et al., Eur. J. Biochem. (1993) vol. 213, 805–814.

"Identification of Multiple Active Growth Factors in Basement Membrane Matrigel Suggests Caution in Interpretation of Cellular Activity Related to Extracellular Matrix Components," by S. Vukicevic et al., Exp. Cell Res. (1992) vol. 202, 1–8.

"Increased Rate of Peripheral Nerve Regeneration Using Bioresorbable Nerve Guides and a Laminin–Containing Gel," by Madison et al., Exp. Neurology (1985) vol. 88, 767–772.

"Isolation and Characterization of type IV procollagen, laminin, and heparan sulfate proteoglycan from the EHS sarcoma," by Kleinman et al., Biochemistry (1982) vol. 21, 6188–6193.

"Formation of a Supramolecular Complex is Involved in the Reconstitution of Basement Membrane Components," by Kleinman et al., Biochemistry (1983) vol. 22, 4969–4974.

"Basement Membrane Complexes With Biological Activity," by Kleinman et al., Biochemistry (1986) vol. 25(2), 312–318.

"Human Laminin Isolated in a Nearly Intact, Biologically Active Form From Placenta by Limited Proteolysis," by Wewer et al., J. Biol. Chem. (1983) vol. 258 (20), 12654–12660.

Rakotoarivony et al., Comptes Rendus Hebdomadaires Des Seances De L'Academie Des Sciences D:Sceinces Naturelles 284(7): 565–568 (1977). (Abstract).

Carlson et al. Renal Physiol. (1980) vol. 3(1–6), 280–287. (Abstract).

Meezan et al. Biol. Chem. Basement Membr., [Proc. Int. Symp.] 1st (1978), Meeting Date 1976, 17–30. (Abstract).

Dixit et al., Artif. Organs 16(4): 336–341 (1992). (Abstract).

Gibbons et al., Eur. J. Biochem. 66(2):243–250 (1976). (Abstract).

* cited by examiner

Primary Examiner—Leon B. Lankford, Jr.
(74) Attorney, Agent, or Firm—Barnes & Thornburg

(57) ABSTRACT

A composition comprising follicle basement membrane is described. The composition can be utilized as a cell culture substrate for proliferating cells in vitro.

11 Claims, 21 Drawing Sheets

F1

F3

F1 (n = 9)

F3 (n = 18)

F5-7 (n = 18)

SYF (n = 18)

F1

F3

F3

F5-7

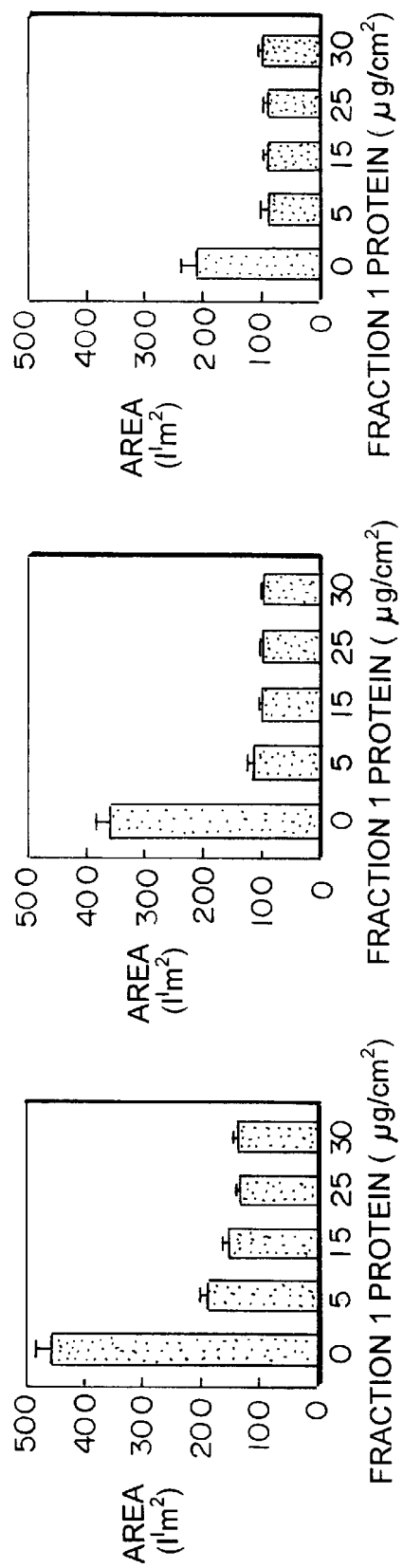
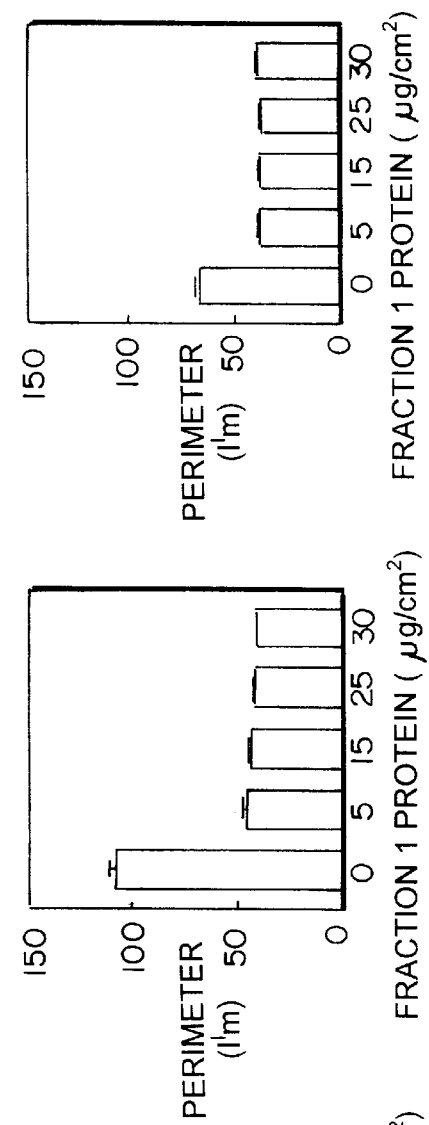
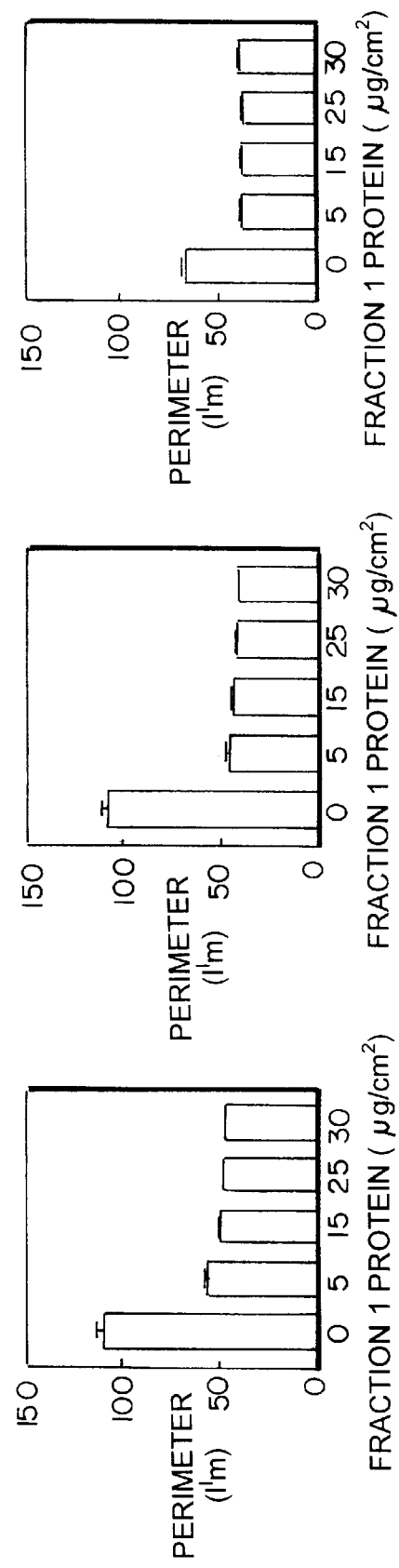

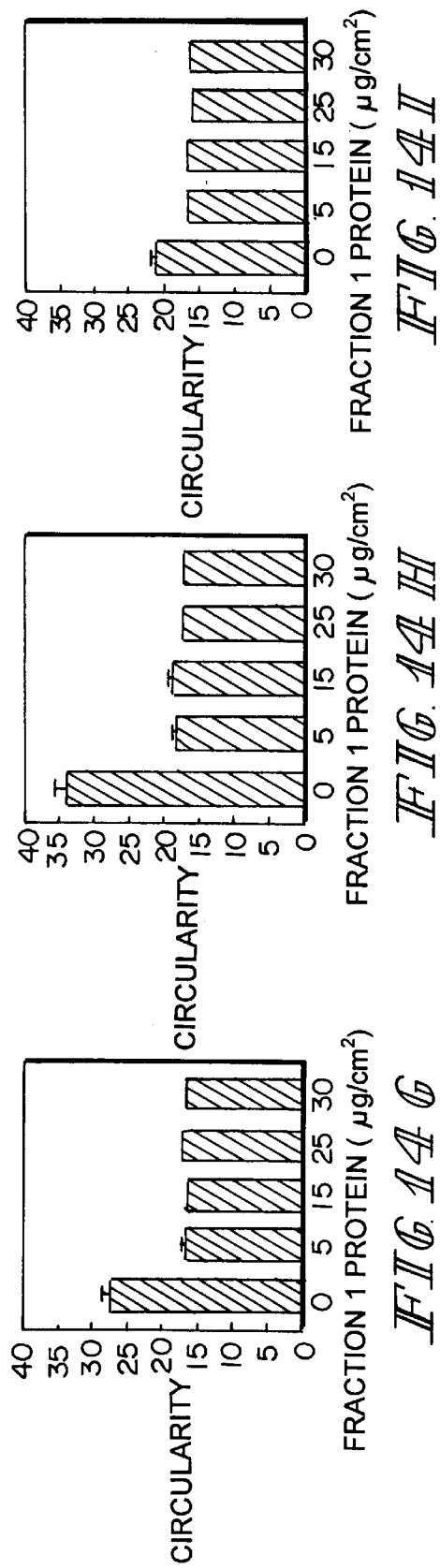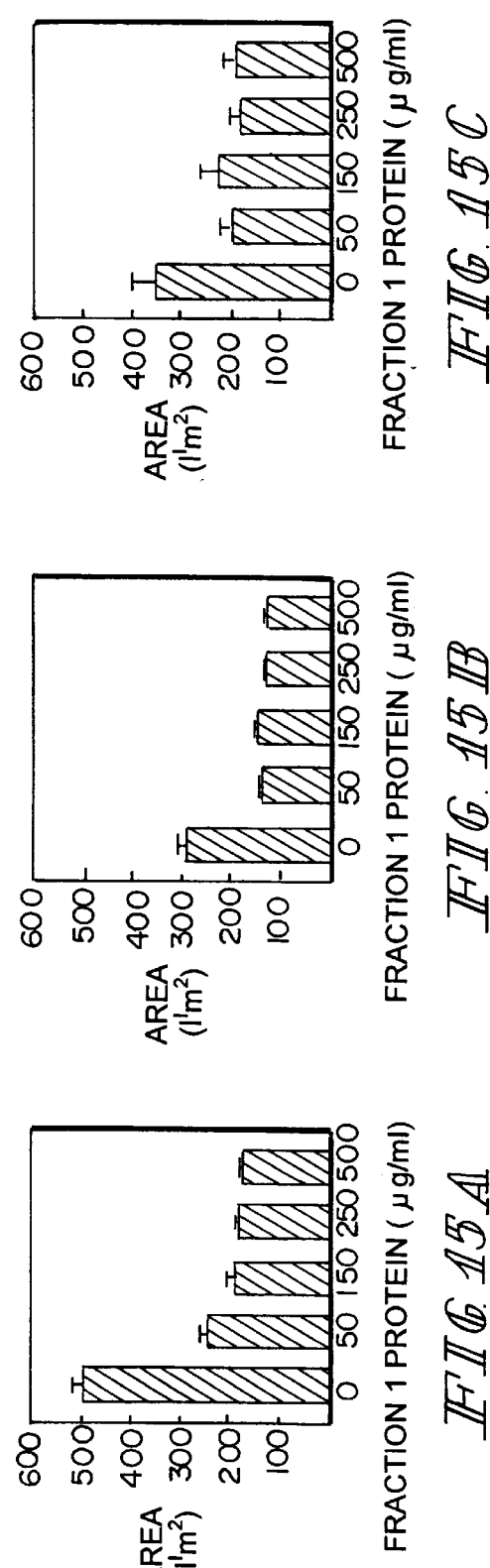

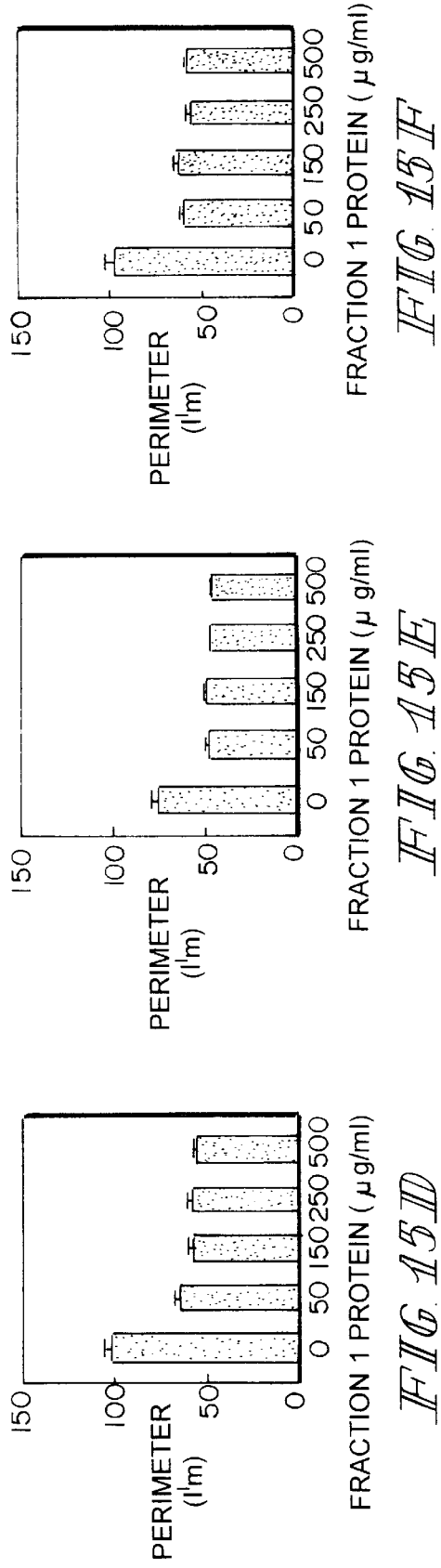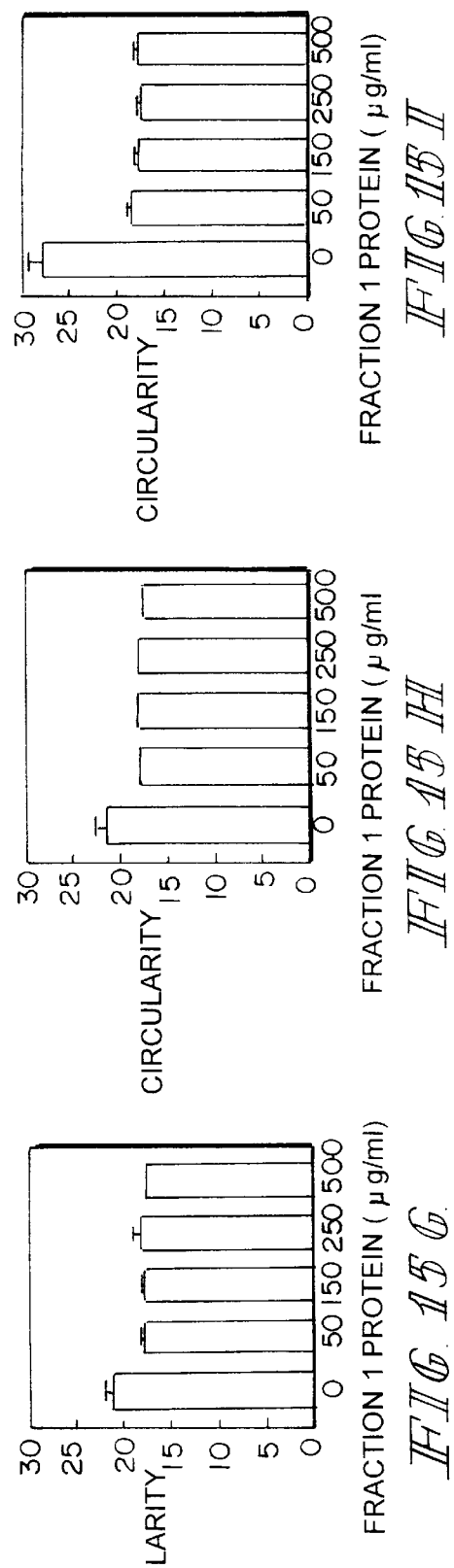

BIOMATERIAL DERIVED FROM FOLLICLE BASEMENT MEMBRANES

CROSS-REFERENCES TO RELATED APPLICATIONS

This application is a U.S. national application of international application Ser. No. PCT/US98/27289 filed Dec. 22, 1998, which claims priority to U.S. provisional application Ser. No. 60/068,769 filed Dec. 23, 1997.

FIELD OF THE INVENTION

The present invention relates to a basement membrane composition and method for its preparation and use. More particularly, the present invention is directed to the basement membrane of avian and reptile follicles and the use of same to support the growth and differentiation of eukaryotic cells cultured in vitro.

BACKGROUND AND SUMMARY OF THE INVENTION

There has been much research effort directed to finding natural and synthetic materials having the requisite properties for use as cell culture substrates. Cellular morphology and metabolic activity of cultured cells are affected by the composition of the substrate on which they are grown. Presumably cultured cells function best (i.e. proliferate and perform their natural in vivo functions) when cultured on substrates that closely mimic their natural environment.

One biological tissue that can potentially be used to culturing cells is the basement membranes of vertebrate tissues. Basement membranes, also known as basal lamina, are extracellular matrices (ECMs) that compartmentalize tissues and provide important signals for the adhesion, growth, differentiation, migration of cells they support. In addition, basement membranes influence several physiological and pathological processes. Accordingly, complete and intact basement membrane is naturally functions as a substrate for cell proliferation and growth. However, intact basement membranes are not commercially available for research.

The ability of complex substrates to support cell growth in vitro has been previously reported, and matrix products supporting such growth are commercially available. For example, Becton Dickinson currently offers two such products: Human Extracellular Matrix, and MATRIGEL® Basement Membrane Matrix. Human Extracellular Matrix is a chromatographically partially purified matrix extract derived from human placenta and comprises laminin, collagen IV, and heparin sulfate proteoglycan. (Kleinman, H K et al., U.S. Pat. No. 4,829,000 (1989)) MATRIGEL® is a soluble basement membrane extract of the Engelbreth-Holm-Swarm (EHS) tumor, gelled to form a reconstituted basement membrane. Both of these matrix products require costly biochemical isolation, purification, and synthesis techniques and thus production costs are high. In addition these matrix products are reconstituted from extracts of basement membranes and thus do not represent the structure of the basement membrane as it exists in the body.

Accordingly, the study of cellular function by culturing cells in vitro is limited by the availability of cell growth substrates that present the appropriate physiological environment for the proliferation and development of the cultured cells.

The present invention is directed to the use of vertebrate basement tissue-derived matrices as substrates for the growth and attachment of a wide variety of cell types. The extracellular matrices for use in accordance with the present invention comprise highly conserved collagens, glycoproteins, proteoglycans, and glycosaminoglycans in their natural configuration and natural concentration. The extracellular matrix is derived from ovarian follicular tissue of a vertebrate species, and in particular ovarian follicular tissue of vertebrate species that lay eggs.

In accordance with one embodiment, a composition comprising intact basement membrane of follicle tissue of a vertebrate is described. The composition comprises basement membrane is substantially free of cells of the source vertebrate wherein the basement membrane is retained in its natural three dimensional shape. Follicle basement membrane (FBM) prepared in accordance with the present invention is use to induce the proliferation and growth of cells. In one embodiment the invention is directed to a composition and method for culturing eukaryotic cells in vitro.

BRIEF DESCRIPTION OF THE DRAWINGS

FIGS. 14A–I Morphometric parameters of granulosa cells incubated in wells pre-coated with fraction 1 of solubilized basal lamina. Graphic representations of the area occupied (FIGS. 14A, 14B and 14C), perimeter (FIGS. 14D, 14E and 14)F and circularity (FIGS. 14G, 14H, and 14I) are shown. Granulosa cells isolated from mature (F1 ; FIGS. 14A, 14D, 14G), developing (F3 ; FIGS. 14B, 14E, 14H), and immature (SYF; FIGS. 14C, 14F, 14I) chicken ovarian follicles were incubated in serum-free medium 199 for 15 hr on plastic or in wells pre-coated with fraction 1 protein (5–50 $\mu$g/cm$^2$). Each point is mean±SEM of 50 or more cells.

FIG. 15 Morphometric parameters of granulosa cells incubated in wells to which fraction 1 of solubilized basal lamina was added as liquid. Graphic representations of the area occupied (FIGS. 15A, 15B and 15C), perimeter (FIGS. 15D, 15E and 15F) and circularity (FIGS. 15G, 15H and 15I) are shown. Granulosa cells isolated from mature (F1.

DETAILED DESCRIPTION OF THE INVENTION

The present invention is directed to an intact basement membrane prepared from vertebrate species and its use for inducing the proliferation and growth of eukaryotic cells. The follicle basement membranes (FBM) of the present invention provide a three dimensional structure that enhances the proliferation and differentiation of eukaryotic cells when placed in an environment conducive to the proliferation of the cells. It has been found that FBM prepared from the follicles of vertebrate species provides a superior substrate for culturing cells in vitro. In particular, cell culture substrates comprising basement membranes prepared from follicle tissue are capable of stimulating cell proliferation and inducing cell differentiation. It is also anticipated that such compositions can be used as biodegradable tissue graft constructs for implantation into vertebrate species.

Figure 1:
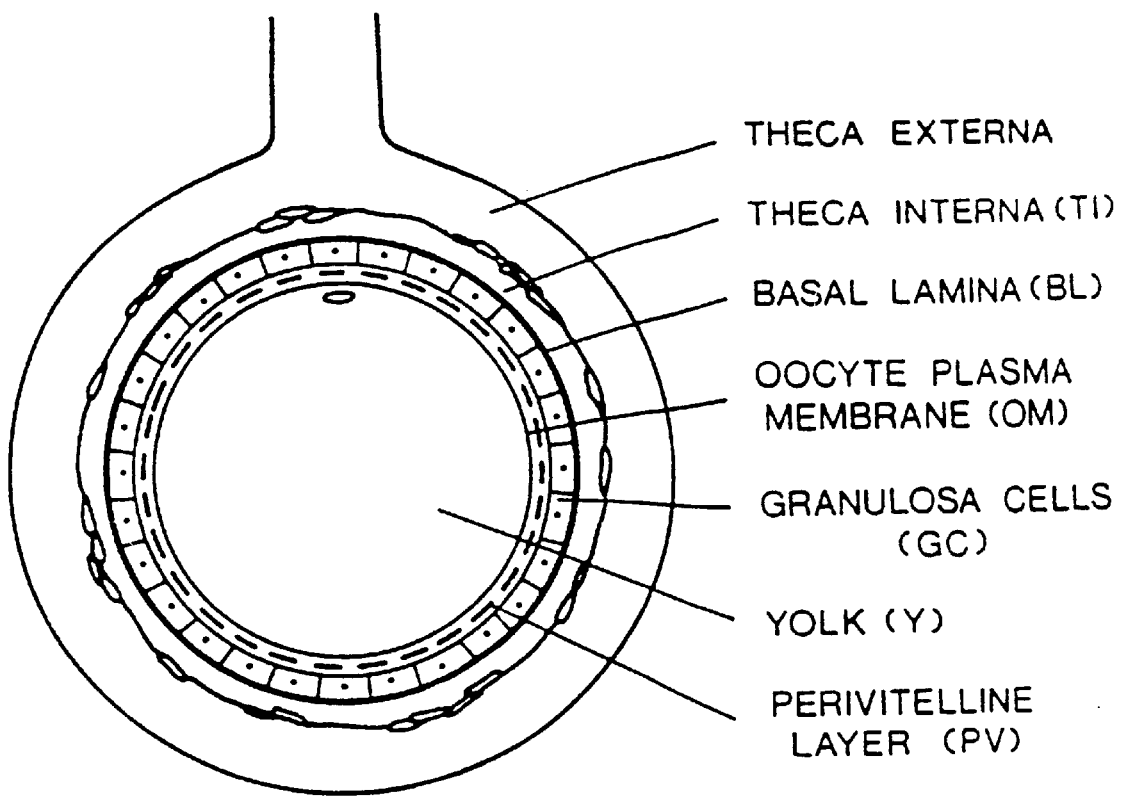
FIG. 1 is a cross-sectional view of a follicle demonstrating the various cell layers of the follicle.

The extracellular matrix prepared in accordance with one embodiment of the present invention comprises basement membranes isolated from the follicle tissues of egg laying vertebrate species including fish, amphibians, reptiles and birds. One preferred source of follicle tissue is the membrana granulosa of avian and reptile species. The membrana granulosa comprises three layers: the Perivitelline layer, the granulosa cell layer and the basal lamina, with the granulosa cell layer located between the Perivitelline layer and the basal lamina (See FIG. 1). The preparation of an extracellular matrix in accordance with the present invention comprises separating the thecal layers from the granulosal layers by the method described by Gilbert et al. (J. Reprod. Fertil. 50:179–181, 1977) and then lysing the cells of the granulosa cell layer to release the Perivitelline layer and basal lamina as intact distinct layers.

Advantageously, the basal lamina of follicle tissue is not attached to connective tissues, and thus can be easily isolated from the other tissue of the membrana granulosa after destruction of the granulosa cells. The preparative techniques described in the present invention provide an extracellular matrix substantially free of any cellular components. More particularly, in one embodiment the extracellular matrix of the present invention comprises intact basal lamina isolated from the membrana granulosa of avian or reptile follicle tissue, substantially free, preferably devoid, of all cells (e.g., the granulosa cells) of the avian or reptile. The basement membrane compositions of the present invention are referred to herein generically as follicle basement membranes (FBM).

In accordance with one embodiment the FBM is prepared from avian ovarian follicle tissues and comprises the basal lamina of the membrana granulosa, and more particularly, the basal lamina prepared from follicle tissue comprises the lamina densa, and the lamina rara. Basement membranes of tissues that are in direct contact with connective tissue may also include a third layer, the lamina reticularis. Since the basal lamina of follicle tissue is not directly attached to connective tissues, the intact basal lamina prepared from follicle tissues is typically devoid of the lamina reticularis layer.

In accordance with one embodiment, basal lamina is prepared from follicle tissue harvested from avian species raised for meat or egg production, including, for example, chickens, turkeys and ostriches. Thus, there is an inexpensive commercial source of follicle tissue for use in preparation of the compositions in accordance with the present invention. Chickens provide one preferred source of follicle tissue for the isolation of intact basal lamina. The structure of chicken ovarian basal lamina is granular in nature, and is similar to that described for the lamina densa layer of basement membranes of rat seminiferous tubule, vas deferens, epidermis, trachea, jejunum; monkey seminiferous tubule, mouse lens capsule, rat Reichert's membrane and rat ovarian basal lamina.

The preparation of follicle basement membrane from follicle tissue of a vertebrate in accordance with the present invention is carried out by removing the cellular components from the tissue. The preparation of the basal lamina from follicle tissues comprises the step of removing the cellular components of the tissue and isolating the intact extracellular matrix. Ideally the process is carried out to separate the cells from the basement membranes without damaging, or at least minimizing disruption or damage to the basement membrane. In accordance with one embodiment the natural three dimensional structure of the original basement membrane matrix is left intact after removal of the cellular components of original follicle tissue. The resulting material comprises an extracellular matrix consisting essentially of follicle basement membrane devoid of endogenous cells associated with the source vertebrate follicle tissue used to prepared the composition.

In accordance with one embodiment basal lamina is isolated from follicle tissue by contacting the follicle tissue with a cell-lysis solution for a time sufficient to lyse/release all cells from the matrix. For example, follicle tissue is treated with a buffer containing 6 M guanidine-HCl, (or 6 M guanidine thiocynate) and shaken overnight at 4° C. The mixture is then centrifuged at 10,000×g and the supernatant is dialyzed against 150 mM NaCl 50 mM, Tris-HCl pH 7.4 overnight at 4° C. and stored frozen in the same buffer. In another embodiment, the tissue is treated with a β-mercaptoethanol (5 mM) solution containing 6 M guanidine-HCl (or guanidine thiocynate) and shaken overnight at 4° C. The mixture is then centrifuged at 10,000×g and the supernatant is dialyzed against 150 mM NaCl, 50 mM Tris-HCl pH 7.4 overnight at 4° C. and stored frozen in the same buffer (solubilized form).

Alternatively the tissue can be treated sequentially, with the guanidine and β-mercaptoethanol solutions. For example, the tissue can be treated with a solution containing 6 M guanidine-HCl and centrifuged to isolate first fraction, comprising basal lamina. The supernatant is kept as a first fraction (fraction 1) and the pellet is then treated with a β-mercaptoethanol (5 mM) solution containing 6 M guanidine-HCl (or guanidine thiocynate) to solubilize a second fraction (fraction 2) comprising basal lamina. The basal lamina can also be prepared in accordance with any of the procedures described above, but substituting 8 M urea for guanidine HCl.

In one embodiment, a composition comprising follicle basement membrane is prepared by suspending the follicle tissue or portions thereof in a cell-lysis solution containing one or more protease inhibitors. After contacting the follicle tissue with the cell-lysis solution for a time sufficient to lyse/release all cells from the matrix, the resulting follicle basement membrane is rinsed one or more times with saline and used immediately or optionally stored in a frozen hydrated state or a partially dehydrated state until used as described below. The cell-lysis step may require several treatments with the cell-lysis solution to release substantially all cells from the basement membrane.

Isolation of intact follicle basement membranes in accordance with the present invention provides an acellular matrix having the three dimensional shape of the natural basal lamina. In one embodiment, the acellular basement membrane matrix comprises basal lamina delaminated from the granulosa cells of avian vertebrate follicle tissue.

In accordance with one embodiment a multi-layered FBM construct is formed by overlapping multiple sheets of follicle basement membrane and adhering the layers to each other. The multi-layered FBM constructs comprising two or more sheets of FBM are preferably formed after the endogenous cells have been removed form the individual FBM sheets. The individual layers can be fix to one another using standard techniques know to those skilled in the art including the use of sutures, staples and biocompatible adhesives such as collagen binder pastes. In one embodiment the layers are fused together by compressing the overlapped regions under dehydrating conditions, optionally with the addition of heat.

In accordance with one embodiment multiple sheets of FBM are completely overlapped with each other to produce a homo-laminate structure having enhanced strength relative to a single sheet of FBM. Alternatively each sheet of the multi-layered construct can be partially overlapped with another sheet of FBM to create a construct having a substantially greater surface area than any one sheet used to form the construct. In accordance with one embodiment each sheet 30–50% of each sheet is overlapped by a neighboring sheet of FBM.

In one embodiment of this invention a fluidized form of FBM is prepared by extracting bioactive components from the FBM or by comminuting and/or enzymatically digesting the prepared FBM. In one embodiment the prepared FBM is frozen and ground to a fine powder, and the powder can be rehydrated to form a fluidized form of the FBM. Alternatively, various components of the FBM can be extracted and solubilized to form bioactive compositions (see Example 3). The viscosity of solubilized basal lamina for use in accordance with this invention can be manipulated by controlling the concentration of the basal lamina component and the degree of hydration. The viscosity can be adjusted to a range of about 2 to about 300,000 cps at 25° C. In addition, the collagen component of the solubilized forms of basal lamina can be polymerized to form a solid or semi-solid matrix using standard techniques known to those skilled in the art (see for example, Kleinman et al., Biochemistry 21: 6188–6193, 1986). For example, high viscosity formulations, for example, gels, can be prepared from the solubilized form of the basal lamina by adjusting the pH of such solutions to about 6.0 to about 8.0 or about 6.5 to about 7.5.

Applicants have discovered that compositions comprising the basal lamina of the membrana granulosa provides a superior cell culture substrate for supporting growth or proliferation of eukaryotic cells in vitro. Accordingly, one embodiment of the present invention is directed to a method for supporting the growth of eukaryotic cells in vitro. The method comprises the step of contacting the cells in vitro with a cell growth substrate comprising basal lamina under conditions conducive to the proliferation of said cells, wherein the basal lamina is delaminated from the membrana granulosa cells of warm-blooded vertebrate follicle tissue. The term "contacting" as used herein with reference to cell culture is intended to include both direct and indirect contact, for example in fluid communication, with the basal lamina composition and the cultured cells. The term "conditions conducive to eukaryotic cell growth" as used herein refers to the environmental conditions, such as sterile technique, temperature and nutrient supply, that are considered optimal for eukaryotic cell growth under currently available cell culture procedures. Although optimum cell culture conditions used for culturing eukaryotic cells depend somewhat on the particular cell type, cell growth conditions are generally well known in the art.

A number of differentiated cell types are still considered difficult to culture (i.e., islets of Langerhans, hepatocytes, chondrocytes, osteoblasts, etc.). It is anticipated that the follicle basement membrane compositions of the present invention can be used to stimulate proliferation of undifferentiated stems cells as well as differentiated cells such as hepatocytes and chondrocytes. Furthermore, the described cell growth composition is believed to support the growth of differentiated cells while maintaining the differentiated state of such cells.

Relative to currently available cell culture substrates derived from extracellular matrices, basal lamina is quick and easy to isolate and advantageously can be used in biomedical research especially in experiments designed to assess the effects of basement membranes exactly in the form in which they exist in vivo. The basal lamina can be used as a cell growth substrate in a variety of forms, including its native intact sheet-like configuration, as a solubilized solution/suspension or gel matrix, as an additive for art-recognized cell/tissue culture media, or as a coating for culture-ware to provide a more physiologically relevant substrate that supports and enhances the proliferation of cells. The membrane material is preferably sterilized prior to use in cell culture applications, however nonsterile material can be used if antibiotics are included in the cell culture system.

The cell growth substrate of the present invention can be combined with nutrients, including minerals, amino acids, sugars, peptides, proteins, or glycoproteins that facilitate cellular proliferation, such as laminin and fibronectin and growth factors such as epidermal growth factor, platelet-derived growth factor, transforming growth factor beta, or fibroblast growth factor. In accordance with one embodiment of the present invention a cell culture substrate comprises the lamina densa delaminated from the Perivitelline layer and granulosa cell layers of follicle tissues of avian and reptilian species. In preferred embodiments the basal lamina is substantially free of follicular cells of the vertebrate source of the basal lamina tissue.

In one embodiment, the intact basal lamina tissue is used as the tissue culture substrate and the cells are seeded directly onto sheets of intact basal lamina under conditions conducive to eukaryotic cell proliferation. In one preferred embodiments the cells are seeded onto the side of the basal lamina that is in contact with the granulosa cells in vivo.

In accordance with one embodiment, fluidized or powder forms of basal lamina are used to supplement standard eukaryotic culture media to enhance the standard media's capacity for sustaining and inducing the proliferation of cells cultured in vitro.

The present basal lamina compositions may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For instance, it is believed that strong gamma radiation may cause loss of strength in the basal lamina.

In accordance with the present invention there is provided a cell culture composition for supporting growth in vitro of an eukaryotic cell population. The composition comprises follicle basement membrane of a warm-blooded vertebrate in combination with nutrients, and optionally including growth factors. The follicle basement membrane can be used with commercially available cell culture liquid media (both serum based and serum free), and the cells can either be in direct contact with the follicle basement membrane or simply be in fluid communication with the follicle basement membrane.

EXAMPLE 1

Preparation of Ovarian Follicle Basement Membrane

Chemicals N-2-hydroxyethylpiperazine-N'-2-ethanesulfonic acid (HEPES), collagenase Type IV, soybean trypsin inhibitor, bovine serum albumin (BSA, Fraction V), penicillin G, streptomycin and fungizone were purchased from Sigma Chemical Co., St. Louis, Mo. Medium 199 (M199) containing Hank's salts was from Gibco-BRL, Grand Island, N.Y.

Animals

Single Comb White Leghorn hens obtained from Purdue University Poultry Research Farms, West Lafayette, Ind., in their first year of reproductive activity, were caged individually in a windowless, air-conditioned room with a 14 hr light: 10 hr darkness cycle. They had free access to a layer ration and tap water. The time of egg lay of each bird in the colony was noted to the nearest 30 min (daily). The animals were killed by cervical dislocation about 10–12 hr before the expected time of ovulation of the largest preovulatory follicle. The first and second largest ($F_1$ and $F_2$) preovulatory follicles were removed and placed in ice-cold Hank's salt solution containing NaCl 144 mM, KCl 5 mM, $MgCl_2$ 1 mM, $CaCl_2$ 1 mM, HEPES 10 mM, pH 7.4. The thecal and granulosal layers were separated by the method described by Gilbert et al. (1977). The granulosa cells were dissociated in medium 199 containing $NaHCO_3$ (350 mg/1), HEPES (20 mmol), pH 7.4, penicillin G (100,000 U/1), streptomycin (100 mg/1), fungizone (250 µg/1), collagenase (500,000 U/1) and trypsin inhibitor (200 mg/1). Cell viability, determined by the trypan blue exclusion method, was routinely greater than 95%.

Isolation of Basal Lamina and Perivitelline Layer

The granulosal layer (membrana granulosa) was placed in a hypotonic solution containing Tris-HCl 10 mM (pH 7.4), leupeptin 0.5 mg/lit, EDTA-$Na_2$ 1 mM, pepstatin 0.7 mg/lit, and phenylmethylsuffonyl fluoride (PMSF) 0.2 mM in a petri dish. The granulosa cells, sandwiched between the basal lamina and perivitelline layer were lysed and the basal lamina and perivitelline layer were separated. The length of time required for the complete separation of the two layers (basal lamina and perivitelline layer) is dependent upon the hypotonicity of the solution. The separation was much faster (1–3 minutes) in the absence of Tris-HCl than in Tris-HCl-containing solution (4–8 minutes). This basal lamina of avian ovarian follicle preparation is intact and comprises the complete basal lamina. The side of basal lamina in contact with granulosa cells is referred to as "granulosa-side" and the side in contact with thecal tissue was assigned the name "theca-side".

Preparation of Basal Lamina-Containing Dishes for Cell Culture

Basal lamina isolated from the largest (32–35 mm in diameter) or second (27–30 mm in diameter) largest preovulatory follicles ($F_1$ and $F_2$) was spread (granulosa side up) in 35 mm Falcon or Corning culture dish and allowed to dry opened to room air in a lamina flow hood at room temperature (23° C.) for 2 hr. The plates were then used following the attachment procedure or were wrapped in aluminum foil and stored in a dessicator kept at 4° C. We did not observe any significant difference between the effects of basal lamina used 2 hr following isolation or basal lamina stored at 4° C. until used. The storage of basal lamina coated culture dishes at room temperature (23° C.) or at 4° C. for two years had no apparent effect on the ability of the matrix material to influence cell morphology.

Cell Culture

Chicken granulosa cells were isolated by collagenase dispersion as described by Novero and Asem Poultry Sci. 72:709–721, 1993). NIH-3T3 fibroblasts (NIH-3T3 cells) and ras-transformed NIH-3T3 cells (ras-3T3 cells), canine prostate cancer cells and human kidney carcinoma cells (A4982 cells) were kindly provided by Dr. David Waters, Department of Veterinary Clinical Sciences, Purdue University, West Lafayette. Cells isolated from chick or rat embryo nervous system were kindly provided by Dr. Jim Walker, Department of Basic Medical Sciences, Purdue University, West Lafayette.

The cells were cultured in medium 199 containing Hank's salts, penicillin G 100.000 U/L, streptomycin 100 mg/L, fungizone 250 $\mu$g/L, Hepes 20 mM (pH 7.4), and BSA 0.1%. Unless indicated otherwise, all cells were cultured in serum-free media and without any other additive.

Confocal Microscopy

Confocal measurements were made on a Bio-Rad MRC 1024 UV/vis confocal scope (Bio-Rad, Inc. Hercules, Calif.) with a Nikon 300 inverted microscope. The images were collected via a 20× objective (differential interference contrast optics). Culture dishes were placed on the Nikon 300 inverted microscope stage and imaged directly. The images were collected using 488 nm light from a Krypton-Argon laser and a frequency matched detector. Some images were electronically magnified via the Lasers lamp 1024 software.

Transmission Electron Microscopy

Granulosa cell layer (granulosa cells, basal lamina, perivitelline membrane) or isolated basal lamina or perivitelline membrane was fixed in 3% glutaraldehyde in 0.15 M Millonig's phosphate buffer pH 7.2 for 24 hr. The layer was then rinsed in phosphate buffer and postfixed in 1% osmium tetroxide-1.5% potassium ferrocyanide at 4° C. for 1.5 hr. Tissue was then rinsed in buffer, dehydrated through a graded ethanol series, rinsed 2× in propylene oxide and infiltrated with epoxy resin (Poly/Bed 812, Polysciences, Warrington, Pa.). After resin polymerization at 60° C. for 48 hr, thin sections (70 nm) were stained with uranyl acetate and lead citrate and examined in a JEOL JEM-100CX transmission electron microscope.

Scanning Electron Microscopy

Granulosal layer (granulosa cells, basal lamina, perivitelline membrane) or isolated basal lamina or perivitelline membrane was fixed in 3% glutaraldehyde in 0.15 M Millonig's phosphate buffer pH 7.2 for 24 hr. The tissue was then rinsed in phosphate buffer and postfixed in 1% osmium tetroxide-1.5% potassium ferrocyanide at 4° C. for 1.5 hr. Tissue was then rinsed in buffer, dehydrated through a graded ethanol series, and then a graded freon 113 series. The granulosa cell layer or the individual components were then picked up from a petri dish containing freon 113 with a glass microscope coverslip and air dried. The coverslips were glued to aluminum stubs with silver paint, sputter coated with gold, and examined in an ISI 100A scanning electron microscope.

RESULTS

Scanning and transmission electron micrographs of cross-section of granulosal layer of a mature preovulatory chicken follicle (35 mm in diameter). The single layer of compressed cuboidal granulosa cells located between the perivitelline layer and basal lamina are separated by intercellular spaces, however, they are connected by cellular projections or cytoplasmic extensions. Microvilli-like extensions could also be observed at the apical portions of some of the granulosa cells. The perivitelline layer in the preovulatory follicle contains a network of thick fibers that appear as electron dense elongated rods when examined by transmission electron microscopy. The basal lamina appears to be made up of a network of fuzzy strands that are irregularly arranged and are separated by spaces. Similar structures (fuzzy strands) or arrangements have been reported in basement membranes and are referred to as cords in the scientific literature (see Inoue and Leblond, 1988). The structure of both basal lamina and perivitelline layer appeared to be unaltered following isolation by the procedure described in materials and methods.

EXAMPLE 2

Influence of Basal Lamina on the Morphology of Cells in vitro

The effect of basal lamina on cell morphology was assessed by observing the morphology of cells cultured in vitro on basal lamina attached to the bottom of 35 mm culture dishes. Cells were plated on Falcon or Corning 35 mm dishes that did not contain basal lamina served as controls.

Hen Granulosa Cells

Within 2 hr of seeding in serum free medium 199, chicken ovarian granulosa cells (freshly isolated) were spread and flattened on plastic. By comparison, granulosa cells plated on basal lamina appeared spherical in shape and were close together in a monolayer; they had a morphology of a similar nature to the shape of chicken granulosa cells in vivo (in intact membrana granulosa). These differences in morphology of granulosa cells were more dramatic in cells cultured for 24 hr. Although granulosa cells which were attached to plastic (adjacent to basal lamina tissue) in basal lamina-containing culture dish were also flattened, they were much less flat than cells in the control dishes. On basal lamina, granulosa cells cultured for only 2 hr were less rounded that those cultured 24 hr.

NIH-3T3 Fibroblasts (NIH-3T3 cells)

Within 2 hr of plating on the control plates, sparsely seeded fibroblasts (NIH-3T3 cells) were attached and exhibiting a flattened shape on the plastic control dishes in serum free medium 199. The cells extended cellular projections and there was little or no cluster formation (aggregation). In contrast, the NIH-3T3 cells that attached to basal lamina were rounded; some were oval in shape (much less elongated) with few or no, cellular projections. Compared to the highly flattened, spindly morphology of cells on the control dish plastic, the NIH-3T3 cells that attached to plastic in basal lamina-containing dishes were less elongated.

Ras-transformed Fibroblasts

Within 2 hr of plating on the control plates, sparsely seeded ras-transformed fibroblasts (ras-3T3 cells) were elongated, and exhibited a spindly and flattened shape on the plastic control dishes. In addition, well defined long cellular projections were observed in control dishes and there was little or no cluster formation (aggregation). In contrast, the ras-3T3 cells that attached to basal lamina appeared oval in shape (much less elongated) with few or no cytoplasmic extensions. Some of the cells were spherical in shape. The ras-3T3 cells tended to aggregate, others formed overlapping clusters on FBM Some of them appear to have penetrated and become situated beneath the FBM Compared to the highly flattened, spindly morphology of cells on the control dish plastic, the ras-3T3 cells that attached to plastic in basal lamina-containing dishes were less elongated.

Canine Prostate Carcinoma Cells

Sparsely seeded canine prostate cancer cells (Chevy LM cells) attached and began to spread on basal lamina as early as 10 min following seeding. No attachment to plastic was observed for at least 30 min. They behaved similarly on both plastic and basal lamina. They adhered firmly to both plastic and basal lamina and were spread with two to three pseudopodial extensions/projections on both basal lamina and plastic after 8–24 hr incubation. Some of the Chevy LM cells were starlike while others were oval in shape on plastic as well as on basal lamina. The projections of some of the cells were placed below the basal lamina. Indeed some of the cells appear to have penetrated and become situated beneath the basal lamina. Although sparsely seeded, the Chevy LM cells tend to form aggregates on both plastic and matrix material.

Human Renal Carcinoma Cells

After 8–24 hr incubation, sparsely seeded human renal carcinoma cells (A4982 cells) spread and became flattened on plastic while those on basal lamina were rounded. A4982 cells extended pseudopods on plastic but not on BLM.

Cells from Nervous System of Chick Embryos

Mixture of cells isolated from the nervous system of eight-day chick embryos were plated in medium 199 supplemented with fetal calf serum. Following 15 hrs in culture, very few cells attached to plastic of control dishes. A few cells were spread and highly flattened and were presumed to be glial cells. Other cells, rounded (and presumed to neuronal cells) were attached to the flattened glial cells. There was no attachment of the rounded cells to plastic in control dishes. Similar to control dish, glial cells that were attached to plastic in the basal lamina-containing dish were spread, flattened and associated with rounded neuronal cells. More cells attached to plastic in basal lamina containing dishes than to plastic in control dishes. Significantly greater numbers of cells were attached to basal lamina than to the plastic. Both glial and neuronal cells interacted firmly with the matrix material. After 15 hr incubation, most of the cells attached to basal lamina were rounded or oval in shape. Some of the oval shaped cells formed what appeared to be chains of cells (three or more cells) connected by cellular projections. Other oval shaped cells extended three or more projections. It was not readily apparent whether the rounded cells on basal lamina were associated with glial cells or not. The number of oval cells (neurons) with two or more elongated cellular projections increased by 24 hr, 48 hr and 84 hr after seeding. By 60 hr after plating, the neuronal cells plated on basal lamina had significantly more and longer processes than in control dishes. The glial cells were multipolar spindle shaped and highly spread on plastic. They appeared to cover less area and were somewhat rounded on basal lamina. After 12 to 19 days in culture, the entire surface of basal lamina was covered by glial and neuronal cells. However this was not true for plastic in either control or matrix containing dishes.

Cells from Cerebellum of Rat Embryos

Mixture of cells isolated from the cerebellum of 17-day rat embryos were plated in medium 199 supplemented with fetal calf serum (10% vol/vol). After 20 hrs in culture, very few cells attached to plastic of control dishes. A few cells were spread and highly flattened and were presumed to be glial cells. Other cells, rounded (and presumed to be neuronal cells) were attached to the flattened glial as well as to basal lamina directly. Attachment of neuronal cells to plastic did not occur. Some of the neuronal cells were unipolar, bipolar or tripolar. By 36 hr the neuronal cells extended very long processes across BLM. Some of the long processes had growth cone-like endings. Such projections did not occur from cells attached to plastic.

EXAMPLE 3

Solubilization of Ovarian Follicle Basement Membrane

Two-Step Solubilization

First Step (Basal lamina First-Fraction)

Avian basal lamina was solubilized in buffer containing 6 M guanidine-HCl, (or guanidine thiocynate) 50 mM Tris-HCl pH 7.4. Following shaking at 4° C. overnight intact pieces of membrane could be seen. The mixture was centrifuged at 10,000×g. The supernatant (first-fraction or basal lamina extract 1) was placed in a 3 kD cutoff dialysis membrane dialyzed against 150 mM NaCl 50 mM, Tris-HCl pH 7.4 overnight at 4° C. The first-fraction (Basal lamina extract 1) was stored frozen in the same buffer.

Second Step (Basal lamina Second Fraction)

The 10,000×g precipitate made up of basement membrane fragments were solubilized with ($\beta$-mercaptoethanol (5 mM) containing 6 M guanidine-HCl (or guanidine thiocynate), 50 mM Tris-HCl pH 7.4 with shaking overnight at 4° C. (second-fraction). The second-fraction is placed in a 3 kD cutoff dialysis tube and dialyzed against 150 mM NaCl, 50 mM Tris-HCl pH 7.4 overnight at 4° C. The dialysate was stored in the same buffer.

With these two steps, the entire avian basal lamina was completely solubilized. Similar results were obtained when 8 M urea was substituted for guanidine HCl. Exclusion of mercaptoethanol from the solubilization buffer led to incomplete solubilization of the Basement membrane (membrane fragments remained). The dialysate became cloudy presumably due to the precipitation of some proteins. The dialysate of second fraction was less cloudy than that of the first fraction.

One-step Solubilization of Basal Lamina

Avian basal lamina was solubilized in one step in buffer containing 6 M guanidine-HCl, 50 mM Tris-HCl pH 7.4, and having 5% $\beta$-mercaptoethanol added. Following 60 min shaking at 4° C., the entire basement membrane was dissolved. Similar results were obtained when 8 M urea was substituted for guanidine-HCl. Exclusion of mercaptoethanol from the solubilization buffer led to incomplete solubilization of the basement membrane (some membrane fragments remained). A longer period of time was required for complete membrane solubilization when a more dilute solution of guanidine-HCl or urea was used. The membrane appeared to be completely solubilized after overnight shaking at 4° C. in mercaptoethanol containing 2 M guanidine HCl or 2 M urea solution. When the material was observed under a light microscope, the 2 M guanidine-HCl-solubilized or 2 M urea-solubilized mixture was clear. The guanidine-HCl or urea-solubilized mixture was dialyzed against 150 mM NaCl, Tris-HCl pH 7.4 at 4° C. overnight, however, the dialysate became cloudy.

EXAMPLE 4

SDS-Page Profile-of Solubilized Basal Lamina Fractions

The solubilized avian basal lamina was resolved by SDS-PAGE on gradient gels (4–20%) as well as on high (12.5%), medium (7.5%) and low (5%) polyacrylamide containing gels and stained with coomassie blue or silver stain. Proteins in avian basal lamina solubilized in one step and avian basal lamina solubilized in two-steps (first- and second-fractions) were resolved.

There were differences between the number and apparent molecular weights of proteins in the first- and second-fractions. The first-fraction contained more bands (with coomassie blue staining) than the second one. In the first-fraction, the range of mol. wt of the proteins is from 10 kDa to 1000 kDa. The range of mol. wt of the proteins in the second-fraction is from 40 kDa to 1000 kDa; most of them are between 40 kDa and 130 kDa. Some proteins present in the second-fraction with mol. wt. between 130 kDa and 200 kDa were absent from the first-fraction. Specifically, a 130 kDa protein, the major protein in the second-fraction is not present in the first-fraction. It is noteworthy that the proteins in the second-fraction stain well with coomasie blue but very poorly with silver stain.

Comparison of SDS-Page Profiles of Matrigel and Solubilized Basal Lamina

The proteins in Matrigel or ECM-gel were resolved by SDS-PAGE on 7.5% gels under reducing conditions. The number of bands in the reconstituted Matrigel was significantly less than in avian basal lamina. It was also observed that the basal lamina first fraction contained a greater number of proteins than Matrigel/ECM-gel. It is interesting that most if not all protein bands in Matrigel (stained with coomasie blue) were present in the basal lamina.

Effect of Solubilized Basal Lamina First-Fraction on Cell Shape

Solubilized and dialyzed first-fraction was diluted with Medium 199 (containing Hank's Salts) buffered with HEPES (10 mM, pH 7.4) and supplemented with 0.1% BSA. Two hundred μl of medium 199 containing different amounts of first-fraction was transferred into 24-well culture plates and allowed to dry completely in a laminar flow hood at room temperature. The wells contained 2, 10 or 20 μg first fraction protein (that is 1, 5 or 10 μg first-fraction per cm$^2$). Control wells received medium 199/BSA alone. Four hundred μl of deionized water was placed in each well and allowed to stand at room temperature for 3–5 minutes. The plates were shaken and the water discarded. When dried, a thin, clear/transparent film layer could be seen at the bottom of the protein-containing wells.

Epithelial cells were then seeded in all wells and incubated for 20 hr at 37° C. Cells attached to both plastic (control wells) and proteins in the first-fraction. The cells in control wells were flattened, spread with cytoplasmic extensions. In contrast, the cells in wells that contained the first-fraction were rounded in shape. The extent of rounding was greatest in the 20 μg protein-containing wells and the least rounding of the cells was observed in the 2 μg containing wells. Importantly, the effect of the first-fraction on cell shape is similar to that observed for intact basal lamina.

Deionized water was used to dilute the first-fraction prior to drying in the culture wells. The effects of first fraction treated in this manner on cell shape was identical to the results obtained when diluted in medium 199/BSA. When diluted in deionized water and dried, it was not necessary to rinse the wells prior to cell incubation.

These results demonstrate that purified and intact basal lamina of avian ovarian follicle has a dramatic effect on the morphology of a wide variety of normal and malignant cells derived from different species. The effect of basal lamina on cell shape is evident within 1–2 hr after plating. Indeed, the basal lamina effect was apparent within 15 min for some cells. In a number of cases (eg., chicken granulosa cells, ras-3T3 cells), the cells that attached to plastic in control dishes were more flattened than some of the cells attached to plastic in basal lamina containing culture dishes. The reason (s) for this observation is unknown, however, basal lamina may have released certain substances that could have influenced cell shape. The results also show that structural integrity of the basal lamina isolated from the chicken ovarian follicle is similar to the structure, of this matrix material in vivo.

EXAMPLE 5

Effect of Intact FBM on Cell Shape in Vitro

Figure 2:
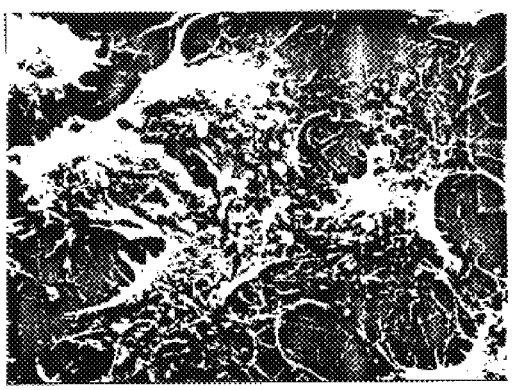
FIGS. 2A and 2B are photomicrographs of fibroblast cells growing on plastic (FIG. 2A) and on FBM (FIG. 2B).
Figure 2:
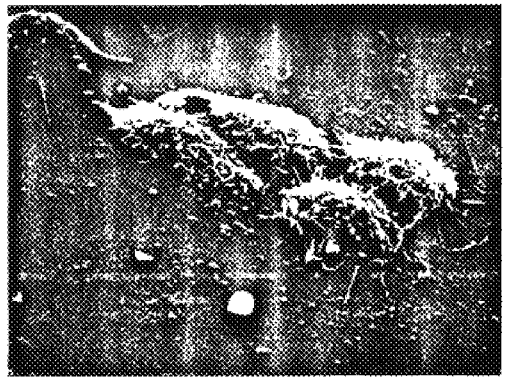
Figure 3:
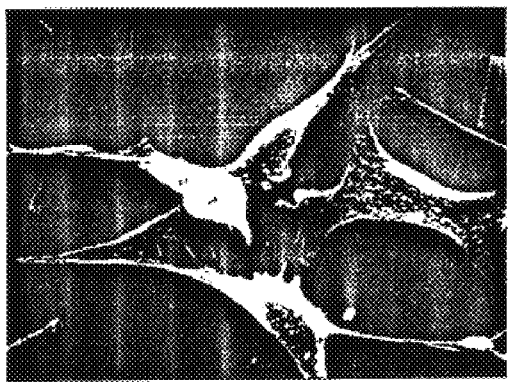
FIGS. 3A and 3B are photomicrographs of epithelial cells growing on plastic (FIG. 2A) and on FBM (FIG. 2B).
Figure 3:
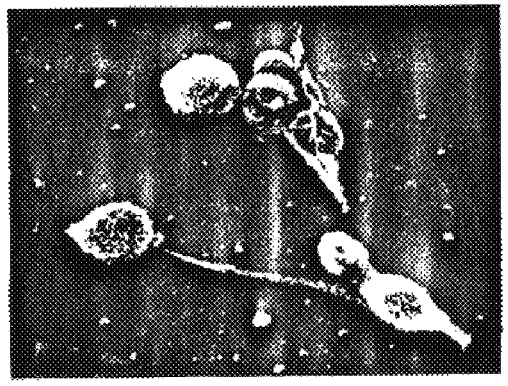

The effect of intact FBM on morphology of cells (obtained from different tissues and species) was assessed in vitro. It was observed that follicle basement membrane can cause normal and malignant cells to adopt a morphology that is distinctly different from that expressed when maintained on plastic (see FIGS. 2 and 3). Importantly, follicle basement membrane can induce normal (in vivo) morphological appearance in different cell types. For example, freshly isolated epithelial cells spread on plastic and became highly flattened (FIG. 2A). By comparison, epithelial cells plated on intact follicle basement membrane were rounded (FIG. 2B). Fibroblasts (NIH-3T3 cells) and ras-transformed fibroblasts (ras-3T3 cells) were flat, elongated with long extensions on plastic (FIG. 3A). However, those attached to follicle basement membrane appeared oval (some were rounded) in shape with few extensions (FIG. 3B). Human vascular endothelial cells and human renal cancer cells (A4982) were also spread and flattened on plastic but became rounded and spherical on follicle basement membrane (data not shown). The storage of follicle basement membrane at 40° C. had no apparent effect on its ability to influence cell shape (data not shown).

EXAMPLE 6

Comparison of SDS-page Profiles of Matrigel and Solubilized FBM

Figure 4:
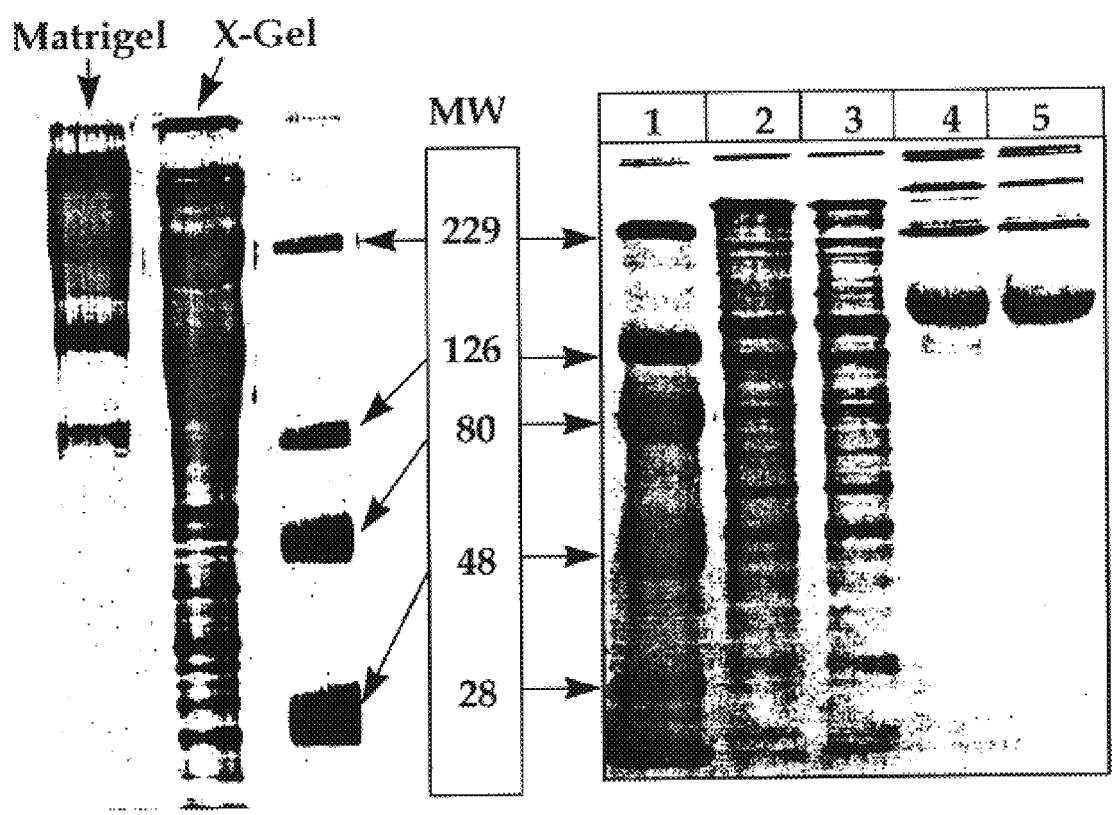
FIG. 4 is an SDS-PAGE profile (7.5% Gel, under reducing conditions) of extracts isolated from Matrigel and from FBM (left panel). The right panel includes various fractions of FBM extracted proteins: lane 1 contains a molecular weight marker; lane 2 the first fraction from batch 1; lane 3 the first fraction from batch 2; lane 4 second fraction from batch 1; lane 5 the second fraction from batch 2.
Figure 5A:
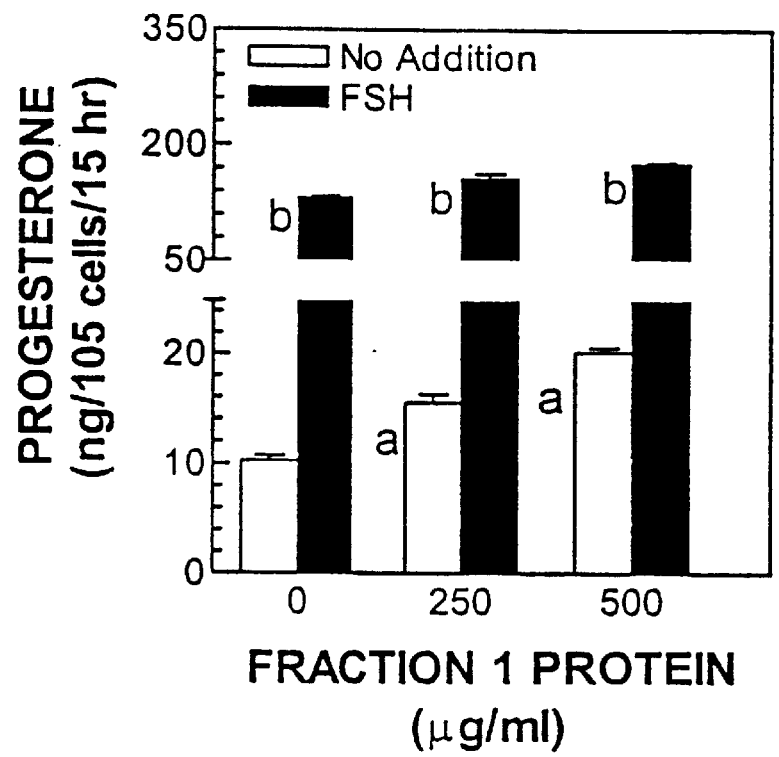
FIG. 5 is a graphic representation of the effect of fraction 1 of FBM on follicle-stimulating hormone (FSH) induced steroid hormone synthesis. Cells that are capable of producing progesterone were placed in tissue culture wells and different amounts of fraction 1 protein was added as a liquid with or without FSH (25 ng/ml). The mixture was incubated for 15 hours (panel A) or 48 hours (panel B) and the amount of progesterone produced was measured. Data are mean±SEM of three incubations. a: $P<0.05$ vs. control (no addition); b: $P<0.01$ vs. no FSH; c: $P<0.05$ vs. no fraction 1, FSH alone. Note the difference in the scale of y axes.
Figure 5B:
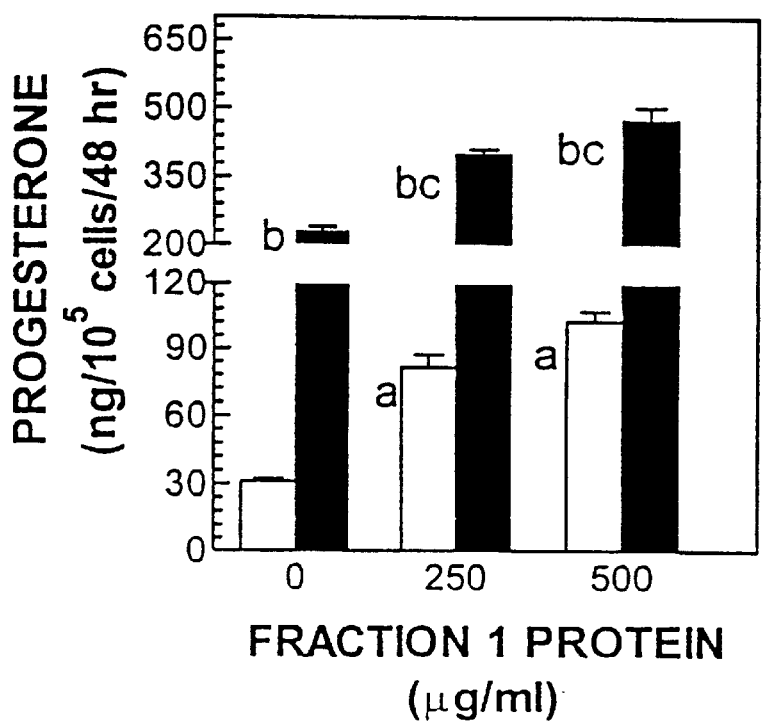

The follicle basement membrane was solubilized in one step with a mixture of guanidine-HCl and β-mercaptoethanol (total extract; FIG. 4A) and designated FBM-Gel. It was also solubilized in two steps: with guanidine-HCl alone (fraction 1) and subsequently with a mixture of guanidine-HCl and β-mercaptoethanol (fraction 2). The solubilized proteins are dialyzed and stored in physiological salt solution buffered with 50 mM Tris-HCl (pH 7.4).

The proteins in FBM-Gel (total extract) as well as proteins in Matrigel or ECM-gel were resolved by SIDS-PAGE on 7.5% gels under reducing conditions. The number of bands in Matrigel/ECM-gel was significantly less than in the FBM-Gel (FIG. 4A). It was also observed that the fraction 1 (of FBM-Gel) contained a greater number of proteins than Matrigel/ECM-gel. Furthermore it is noted that the protein bands in Matrigel were present in the solubilized FBM-Gel.

EXAMPLE 7

Effect of Solubilized Follicle Basement Membrane on Cell Shape In Vitro

Solubilized FBM was prepared in accordance with Example 3. Solubilized first-fraction was diluted with deionized water and different amounts were transferred to tissue culture wells. The protein was allowed to dry completely in tissue culture wells at room temperature. The wells contained 2, 10 or 20 μg fraction 1 protein (that is 1, 5 or 10 μg fraction 1 per $CM^2$). Control wells received deionized water alone. When dried, a clear layer of material could be seen at the bottom of the wells. In wells that contained greater amounts of fraction 1 e.g. 30 μg/$CM^2$ or more, the dried material is slightly cloudy in appearance. However, this did not interfere with studies under the light microscope.

Epithelial cells were then seeded in the wells and incubated for 15 hr at 37° C. The cells in control wells were flattened, spread with cytoplasmic extensions. In contrast, the cells in wells that contained fraction 1 were rounded in shape. The degree of change in shape was dependent on the amount of fraction 1 in the wells. Significant change in cell shape was observed in wells containing as low 1 μg/$cm^2$ fraction 1. Importantly, the effect of the solubilized basement membrane (fraction 1) on cell shape was similar to that observed for intact follicle-basement membrane. Therefore, the follicle basement membrane can be solubilized without any apparent loss of its properties. Importantly, the FBM-Gel allows for the preparation of low cost extracellular matrix that is fully competitive with the available industry standard (Matrigel).

Effect of Solubilized FBM on Cell Function In Vitro

Figure 6:
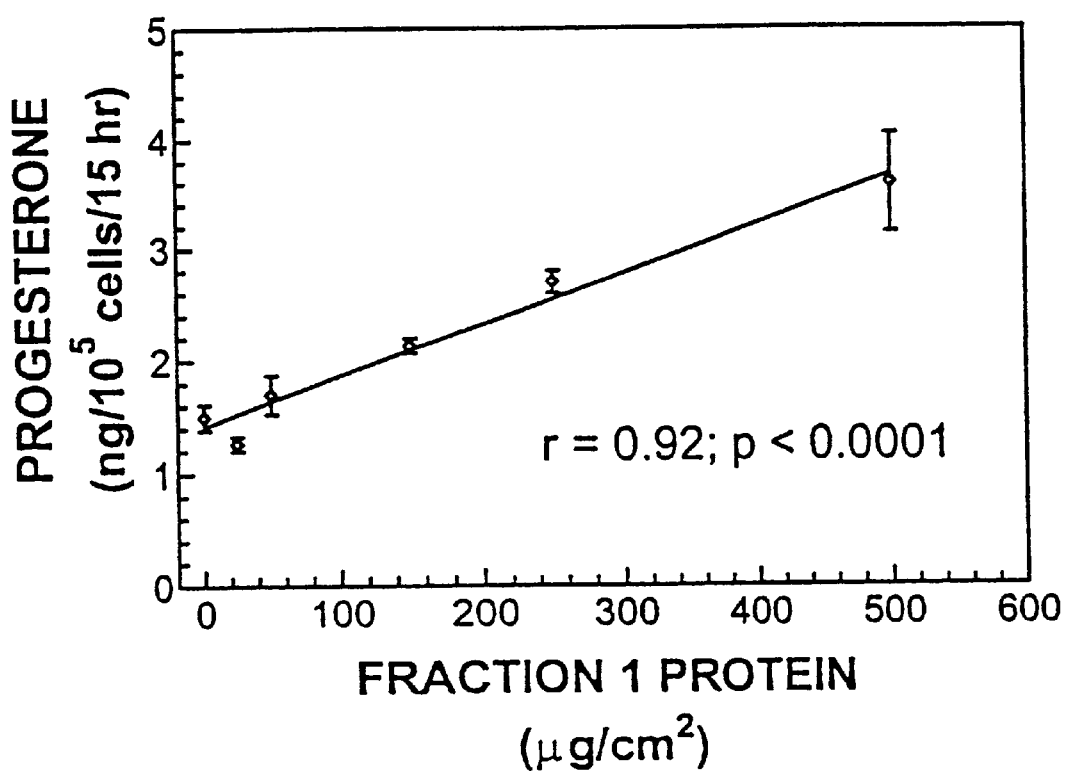
FIG. 6 is a graphic representation of the effect of fraction 1 of FBM on cell function in vitro. Cells that are capable of producing progesterone were placed in tissue wells in which different amounts of fraction 1 had been dried. The cells were incubated for 15 hours and the amount of progesterone produced was measured. Data are mean±SEM of six incubations.
Figure 7A:
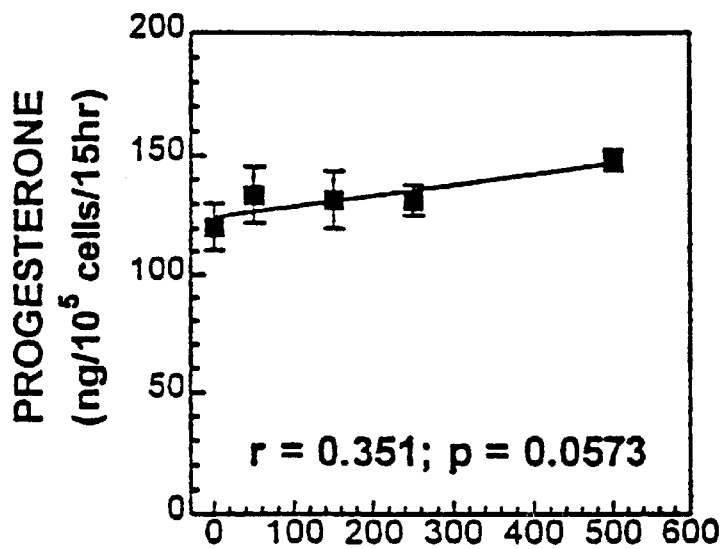
FIGS. 7A–7D Effect of fraction 1 solubilized basal lamina protein (liquid form) on progesterone production. Granulosa cells isolated from immature (SYF), first (F1), third (F3) and developing fifth, sixth and seventh (F5–7) largest preovulatory follicles were placed in 96-well plates and different amounts of fraction 1 were added as liquid. The mixture was incubated for 15 hr and the progesterone content of the incubation medium was measured. Data are mean±SEM of nine incubations from three separate experiments.
Figure 7B:
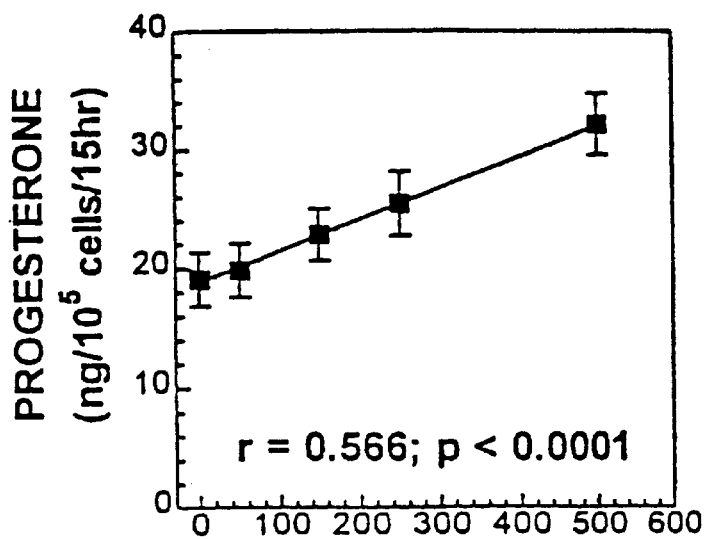
Figure 7C:
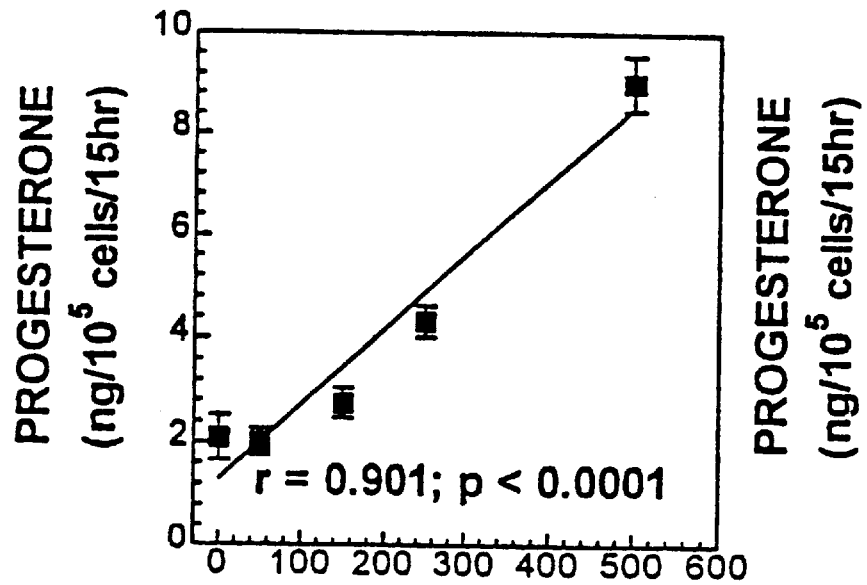
Figure 7D:
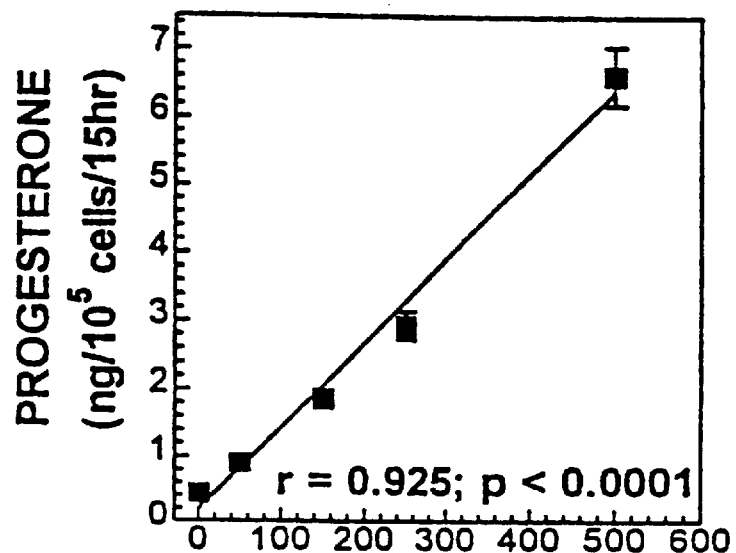

Experiments were conducted to determine if FBM-Gel can influence cell function. Cells capable of producing progesterone (a steroid hormone) were used as a model system to examine the effects of FBM-Gel on cell function. When different amounts (50–500 μg/ml) of fraction 1 were added as a liquid to medium in which the steroid hormone producing cells were incubated, the matrix protein caused an increase in the quantity of progesterone produced in a concentration dependent manner (FIGS. 6A and 6B). In addition, fraction 1 increased significantly follicle stimulating hormone- (FSH-) induced progesterone production by these cells (FIGS. 6A and 6B). FSH is a known stimulator of the functions of these steroid hormone producing cells. These results demonstrated that fraction 1 of solubilized FBM-Gel capable of influencing both basal and stimulated functions of cells.

In certain experiments, the steroid producing cells were incubated in wells in which fraction 1 of FBM-Gel had been dried (10–160 μg/$CM^2$). As observed previously, there was significant increase in progesterone production in fraction 1 containing wells (FIG. 8).

EXAMPLE 8

Identification of Follicle Basement Membrane Components

Using immunoblot techniques (Western blot analysis), polyclonal antibodies raised against mammalian, human and avian proteins cross-reacted with several proteins in solubilized basal lamina. When available commercially, monoclonal antibodies were used. Based on positive reactions with available antibodies, follicle basement membrane contains the following:

Extracellular Matrix Proteins: Fibronectin, tenascin, osteonectin (SPARC or BM-40); type IV collagen, entactin/nidogen, heparan sulfate proteoglycan (HSPG) laminin. Basement membranes (basal lamina) have different proportions of collagen as well as non-collagenous extracellular matrix proteins such as, laminin and heparan sulfate proteoglycans (HSPG). Follicle basement membrane contains fibronectin which is absent from Matrigel/ECM-gel.

Growth Factors: Acidic fibroblast growth factor (aFGF), basic fibroblast growth factor (bFGF), epidermal growth factor (EGF), transforming growth factor-α(TGF-α); insulin-like growth factor-I (IGF-1), insulin-like growth factor-II (IGF-II), platelet-derived growth factor-AA (PDGF-AA); transforming growth factor-β (TGF-β1, -2, -3, -5).

Insulin-like Growth Factor Binding Proteins: Insulin-like growth factor binding proteins (IGFBPs) IGFBP-2, IGFBP-3, IGFBP-4, IGFBP-5, IGFBP-6 and IGFBP-7.

Cytokines/Hematopoietic Factors: Interferon-γ (IFN-γ), interleukin-3 (IL-3), granulocyte macrophage-colony stimulating factor (GM-CSF).

Matrix Metalloproteinases (MMPs): MMP-1, MMP-2, MMP-3, MMP-8, MMP-9 and MMP-13.

Tissue Inhibitors of Matrix Metalloproteinases (TIMPs): TIMP-1, TIMP-2, TIMP-3, TIMP-4.

Plasminogen Activators and their Inhibitors: Tissue-type plasminogen activator (t-PA), urokinase-type plasminogen activator (u-PA) and type 1 plasminogen activator inhibitor (PAI-1). In addition to the above, follicle basement membrane contains other unknown or yet unrecognized proteins (substances).

EXAMPLE 9

Effects of Basal Lamina on Progesterone Production by Ovarian Granulosa Cells

Materials and Methods
Solubilization of Basal Lamina
Fraction 1: Basal lamina was placed in a microfuge tube and solubilization buffer containing 6 M guanidine-HCl, 50 mM Tris-HCl pH 7.4 was added (100 μl buffer per basal lamina per follicle). After shaking at 4° C. overnight some membrane fragments remained. The mixture was centrifuged at 1,000–2,500×g for 10 min. The supernatant designated fraction 1 was placed in a 3 kD cutoff dialysis membrane and dialyzed against 150 mM NaCl 50 mM, Tris-HCl pH 7.4 overnight at 4° C. After dialysis, fraction 1 turned cloudy, presumably due to the precipitation of some proteins. The dialyzed fraction 1 was aliquoted and stored at −70° C. in the same buffer. Fraction 1 forms 80–90% by weight of basal lamina.

Fraction 2: The basal lamina fragments collected by centrifugation were solubilized with 6 M guanidine-HCl, 50 mM Tris-HCl pH 7.4 containing β-mercaptoethanol (5 mM) with shaking for 60 min at 4° C. and designated fraction 2. Similar results were obtained when 8 M urea was substituted for guanidine-HCl. The fraction 2 solution was placed in a 3 kD cutoff dialysis tube and dialyzed against 150 mM NaCl, 50 mM Tris-HCl pH 7.4 overnight at 4° C. The dialysate was aliquoted and stored at −70° C. in the same buffer. The dialysate of fraction 2 did not turn cloudy. The exclusion of β-mercaptoethanol from the solubilization buffer led to incomplete solubilization of the basal lamina (fragments remained).

Preparation of Solubilized Basal Lamina-Containing Dishes for Cell Culture

Fraction 1 of the solubilized basal lamina was diluted with deionized water or modified Hanks salt solution or medium 199. Aliquots of 100–200 $\mu$l containing 10–160 $\mu$g of proteins were transferred into 96-well or 24-well Falcon culture dishes (Fisher Scientific) and allowed to dry under tissue culture hood. These are designated pre-coated wells (solid form of solubilized basal lamina). Some wells received vehicle only and served as controls. Culture wells that received Hanks salt solution or medium 199 were rinsed two times with deionized water prior to the incubation of cells. Tissue isolation, solubilization, dialysis and preparation of culture dishes were carried out under sterile conditions.

Incubation of Granulosa Cells

Incubation of cells in solubilized basal lamina-containing dishes: Collagenase dispersed chicken granulosa cells were plated at a density of 0.5 to 2×10$^5$ live cells/ml in 96-well tissue culture plates in which different amounts of fraction 1 of solubilized basal lamina had been dried (solid form of solubilized basal lamina). The cells were incubated at 37° C. in serum free M199 containing 0.1% (wt/vol) BSA as described by Novero and Asem (1993). In other experiments, granulosa cells, 0.25 to 1×10$^5$ live cells/ml were placed in 96-well Falcon plates (Fisher Scientific, Springfield, N.J.) and different amounts of solubilized basal lamina were added (liquid form of solubilized basal lamina). The mixture was incubated at 37° C. in serum free M199 containing 0.1% (wt/vol) BSA.

Measurement of Progesterone

The progesterone content of incubation media was determined by radioimmunoassay.

Statistical Analyses

Each experiment contained three replicate wells per treatment and was repeated three times unless otherwise noted. The data were analyzed by analysis of variance followed by post-hoc Tukey test to determine significant differences among treatment means. Differences at $P \leq 0.05$ were considered significant.

RESULTS

Effect of Solubilized Basal Lamina on Progesterone Production in Granulosa Cells In Vitro Because basal lamina is in direct contact with granulosa cells in vitro, the effect of fluidized basal lamina on the function of these was assessed. Progesterone is the primary steroid hormone produced by chicken granulosa cells and its production varies with the state of cell differentiation (state of follicular development). The effects of fraction 1 of solubilized basal lamina on progesterone synthesis in chicken granulosa cells, were examined in (1) experiments in which different amounts of fraction 1 were added as liquid (liquid form) to the incubation medium or (2) in experiments in which granulosa cells were incubated in culture wells in which fraction 1 had been dried (solid form).

Liquid Form: Fraction 1 of solubilized basal lamina, added as liquid to the incubation medium caused increase in progesterone production in a concentration dependent manner in granulosa cells obtained from mature (F1), developing (F3, F5–7) and immature (SYF) follicles (FIGS. 7A–D). The slope of the regression line was greater for SYF and F5–7 than for F3 or F1 granulosa cells. This indicates that a unit concentration of fraction 1 caused a greater increase in the quantity of progesterone produced by less differentiated SYF granulosa cells than the amount of progesterone produced by differentiating F3 or differentiated F1 granulosa cells. The stimulatory effect of fraction 1, added as liquid on progesterone production was least in wells that contained F1 cells (FIGS. 7A–D).

Figure 8A:
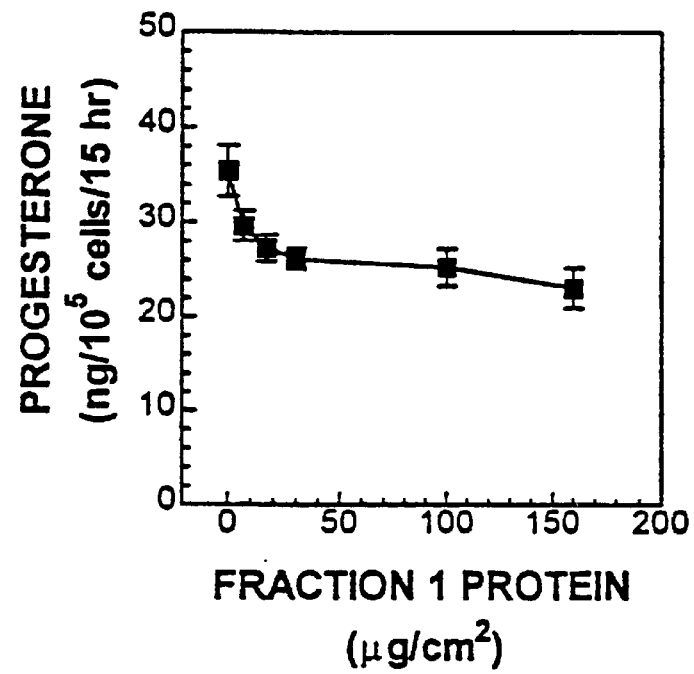
FIGS. 8A–8D Effect of pre-coated fraction 1 (solid form) of solubilized basal lamina on progesterone production. Granulosa cells isolated from immature (SYF), first (F1), third (F3) and developing fifth, sixth and seventh (F5–7) largest preovulatory follicles were incubated in 96-well plate that were pre-coated with different amounts of fraction 1 protein. The cells were incubated for 15 hr and the progesterone content of the incubation medium was measured. Data are mean±SEM of nine incubations from three separate experiments.
Figure 8B:
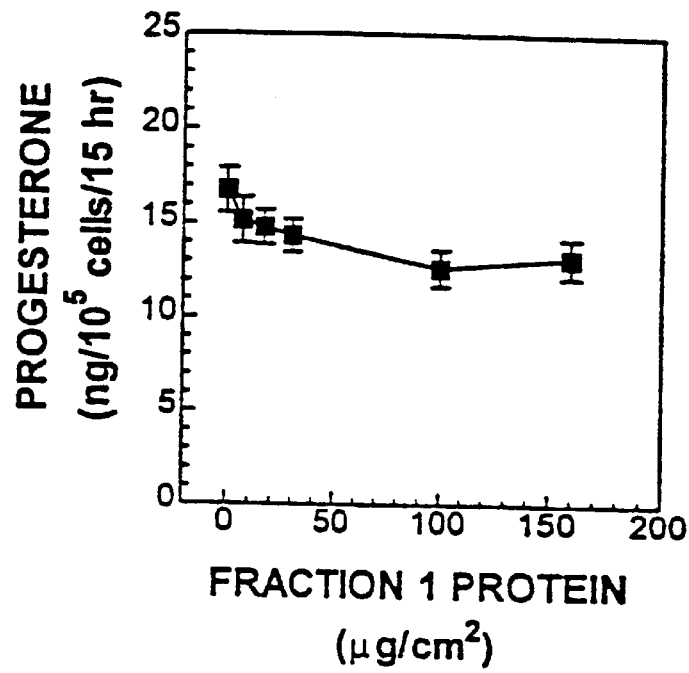
Figure 8C:
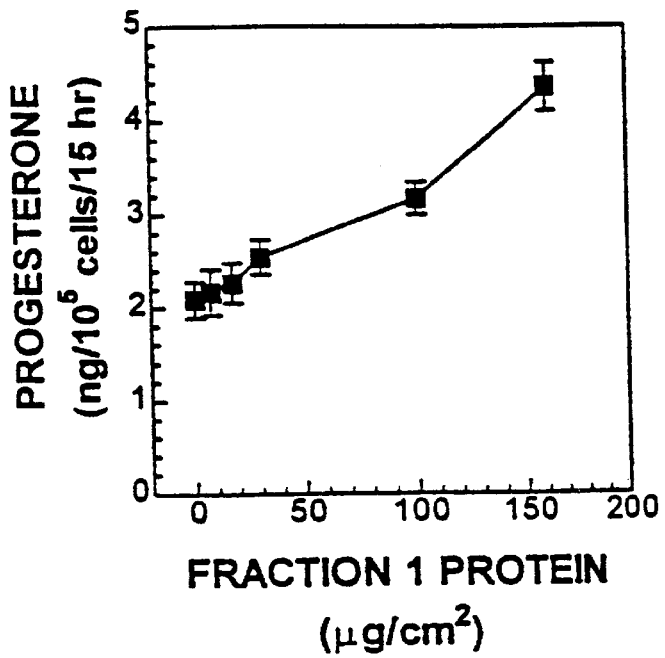
Figure 8D:
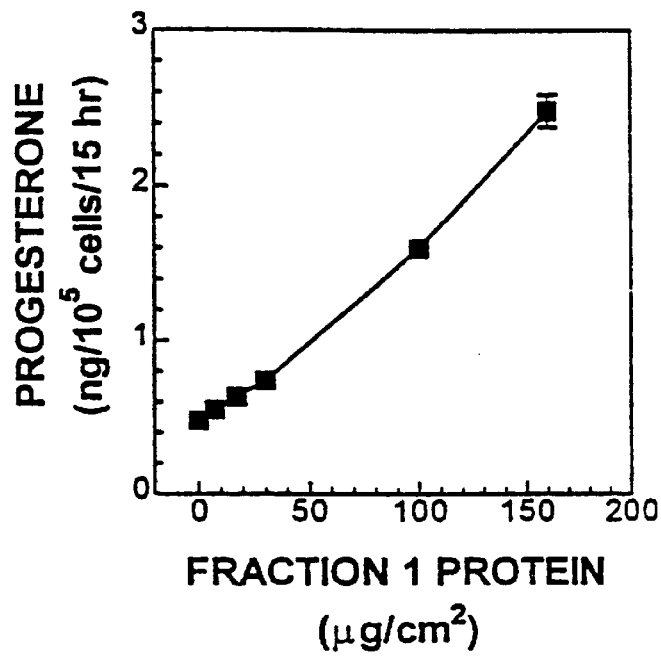

Solid Form: Granulosa cells were incubated in wells in which fraction 1 of protein had been dried (solid form; 10–160 $\mu$g/cm$^2$). In this form, fraction 1 alone caused a dose-dependent decrease in progesterone production by differentiated (F1) and differentiating (F3) cells (FIGS. 8A & 8B); by contrast, fraction 1 alone significantly increased the amount of progesterone produced by less differentiated (F5–7 and SYF) granulosa cells (FIGS. 8C & 8D). These results show clearly that basal lamina regulates granulosa cell function and that its effect is dependent on the state of cell differentiation.

Figure 9A:
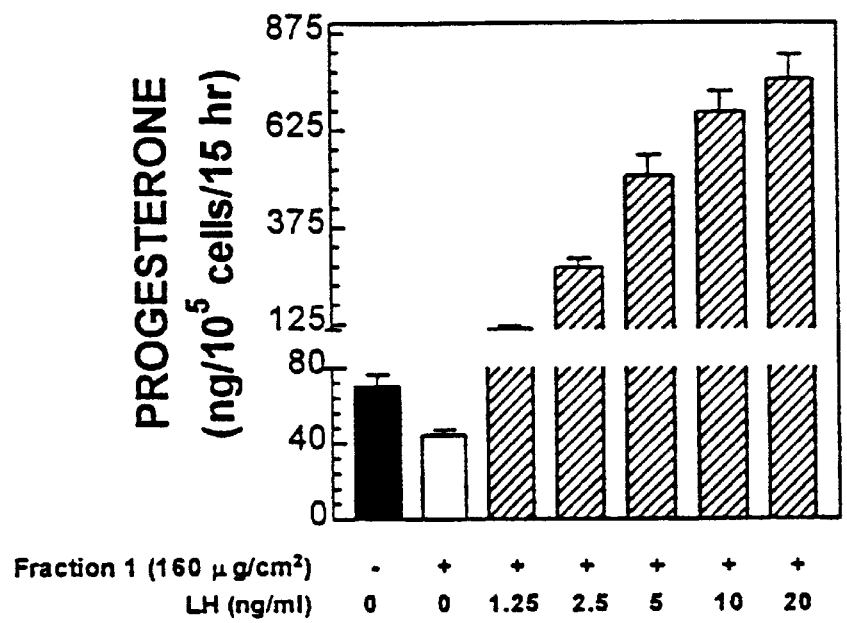
FIGS. 9A–9C Dose-response effect of LH on progesterone production in the presence of the solid form of fraction 1 basal lamina. Granulosa cells isolated from the first (F1), third (F3) and developing fifth, sixth and seventh (F5–7) largest preovulatory follicles were incubated in 96-well plate that were pre-coated with fraction 1 (160 $\mu$g/cm$^2$) of fluidized basal lamina proteins. The cells were incubated for 15 hr in the presence and absence of different amounts of LH and the progesterone content of the incubation medium was measured. Data are mean±SEM of nine incubations from three separate experiments.
Figure 9B:
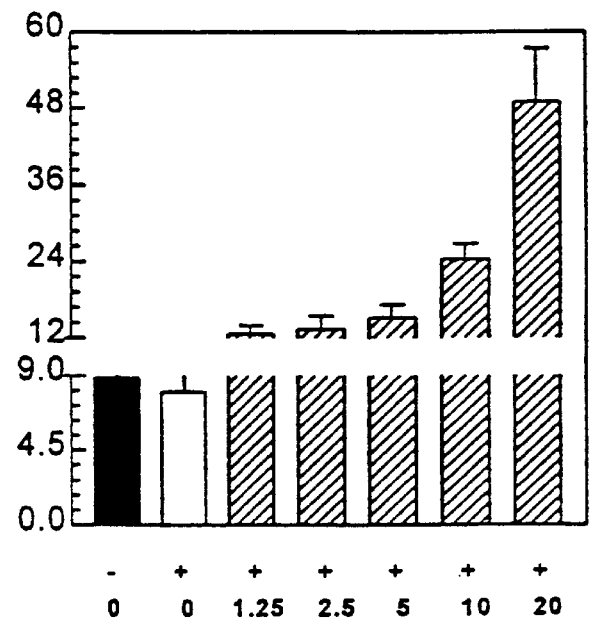
Figure 9C:
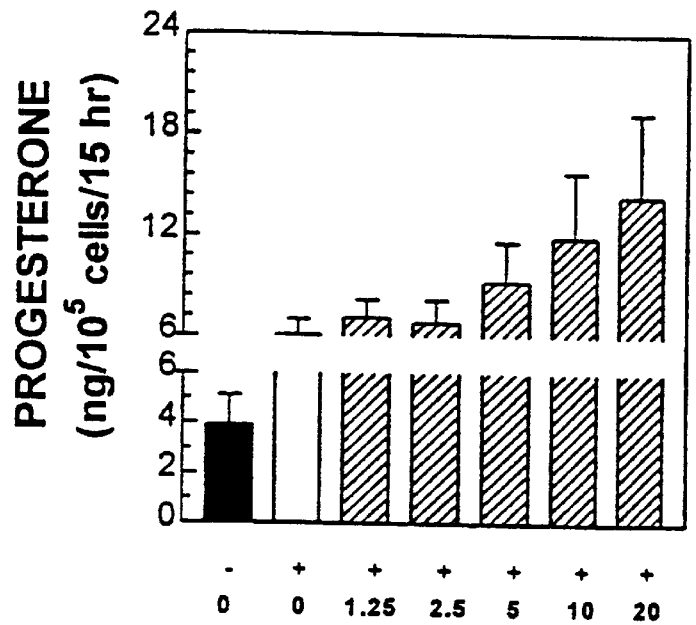
Figure 10A:
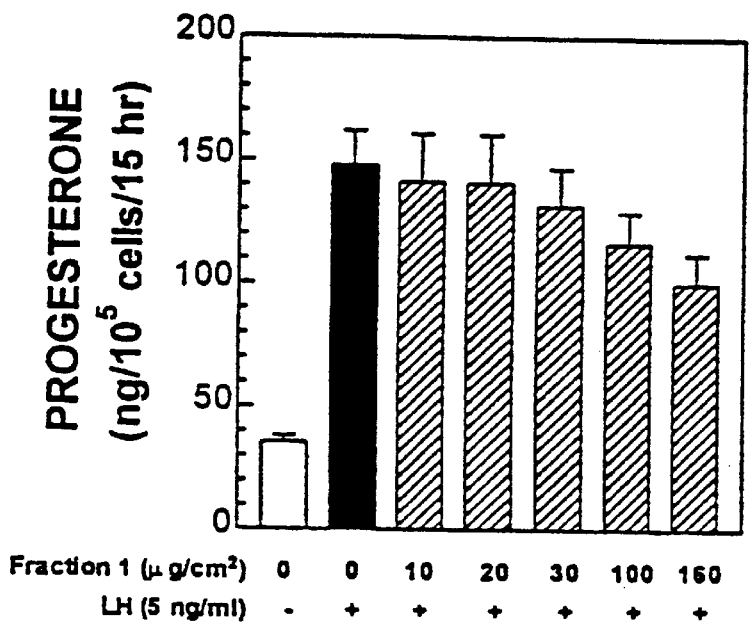
FIGS. 10A–10C Dose-response effect of the solid form of fraction 1 of basal lamina on LH-induced progesterone production. Granulosa cells from the first (F1), third (F3) and fifth, sixth and seventh (F5–7) largest preovulatory follicles were incubated in 96-well plate that were pre-coated with different amounts of fraction 1 of fluidized basal lamina. The cells were incubated for 15 hr in the presence and absence of LH (5 ng/ml) and the progesterone content of the incubation medium was measured. Data are mean±SEM of nine incubations from three separate experiments.
Figure 10B:
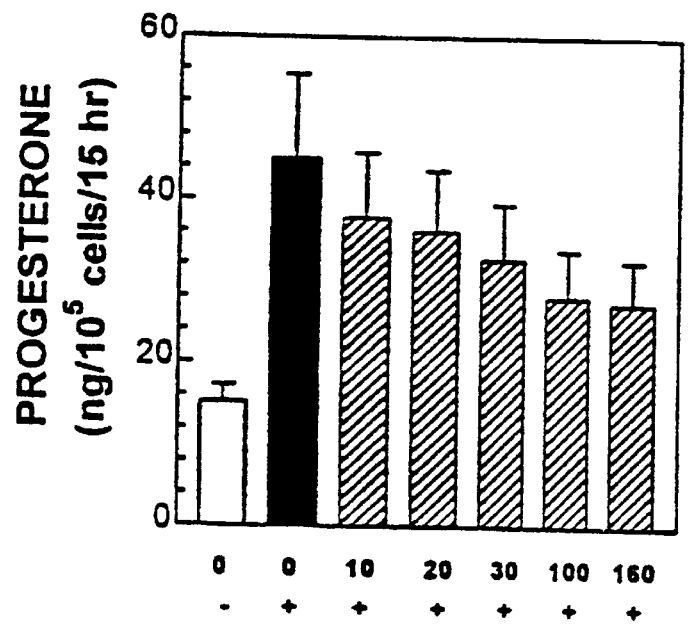
Figure 10C:
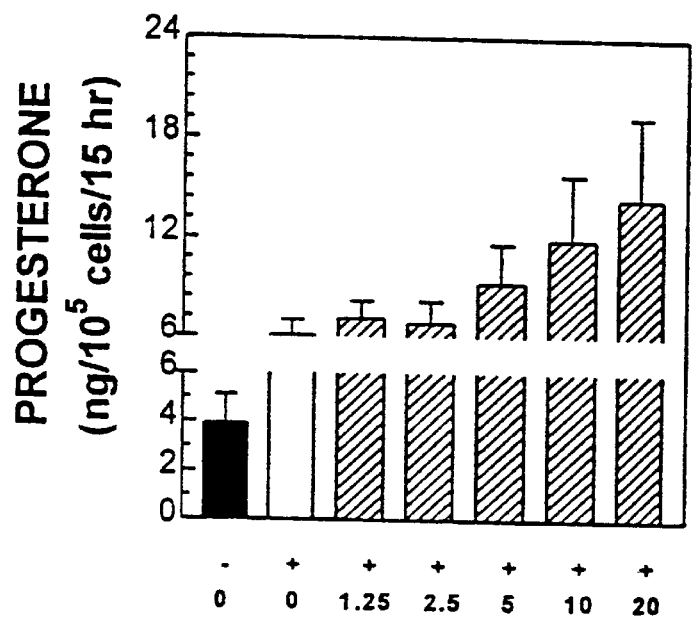

Effect of Solubilized Basal Lamina on LH-induced Progesterone Production In Vitro Experiments were conducted to determine the effects of fraction 1 protein on luteinizing hormone- (LH-) induced steroidogenesis in granulosa cells. LH stimulated progesterone production in a dose-dependent manner, by granulosa cells incubated in culture wells pre-coated with a fraction 1 (FIG. 9). In these experiments, as expected, the solid form of fraction 1 suppressed basal progesterone production in differentiated (F1) cells but increased it in differentiating (F5–7) ones (compare FIG. 9A with FIG. 9C). Additional experiments were conducted to examine further the interactions between the solid form of fraction 1 protein and LH in regulating progesterone production by granulosa cells. The cells were stimulated with a single concentration of the LH in culture wells pre-coated with different amounts of fraction 1. The results shown in FIGS. 10A and 10B demonstrate that dried fraction 1 suppressed LH-induced progesterone production by differentiated (F1) and differentiating (F3) cells in a dose-dependent fashion. By comparison the stimulatory effect of LH in less differentiated (F5–7) cells was not attenuated by solid form of fraction 1 (FIG. 10C). It is noteworthy that the level of progesterone produced in culture wells containing the maximally inhibiting amount of dried fraction 1 was greater than the level of progesterone produced by cells in control wells. The data shown in FIG. 10 suggest that the results in FIG. 9 represent dried fraction 1-subdued LH effects.

Figure 11A:
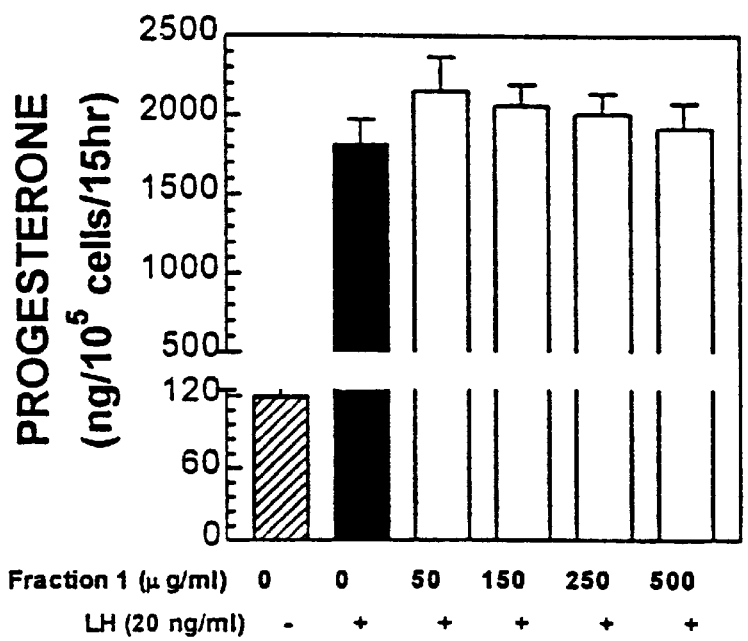
FIGS. 11A–11B Dose-response effect of the liquid form of fraction 1 of basal lamina on LH-induced progesterone production. Granulosa cells from the first (F1), fifth, sixth and seventh (F5–7) largest preovulatory follicles were placed in 96-well plates and different amounts of fraction 1 were added as liquid. The mixture was incubated for 15 hr in the presence and absence of LH and the progesterone content of the incubation medium was measured. Data are mean±SEM of nine incubations from three separate experiments.
Figure 11B:
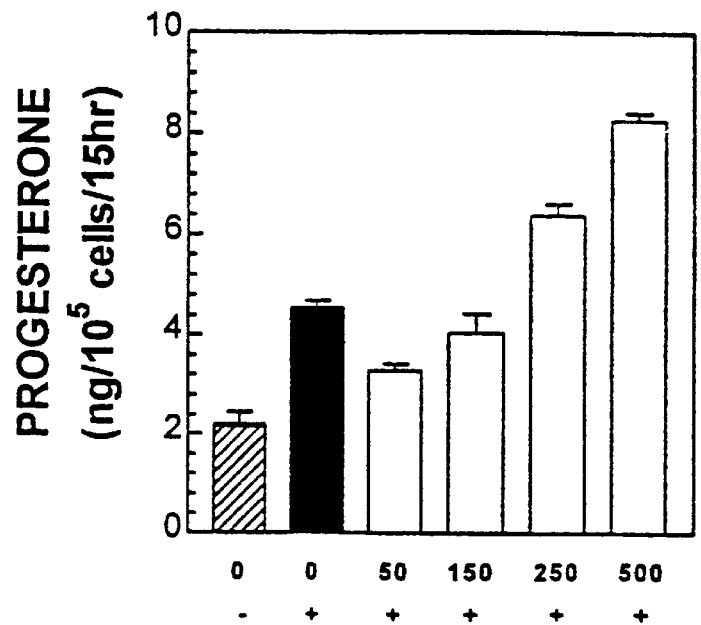

LH interacted with the liquid form of fraction 1 as well. In the liquid form, fraction 1 protein did not suppress the stimulatory action of LH (FIGS. 11A and 11B) irrespective of the state of granulosa cell differentiation. The stimulatory effect of LH on progesterone production in both differentiated (F1) and differentiating (F5–7) granulosa cells was further enhanced (albeit marginally) by the liquid form of fraction 1 (FIGS. 11A and 11B). The amount of progesterone production caused by LH was greater in granulosa cells from mature (F1) follicles than in granulosa cells in developing (F3 or F5–7) cells (FIGS. 9, 10 & 11).

Figure 13A:
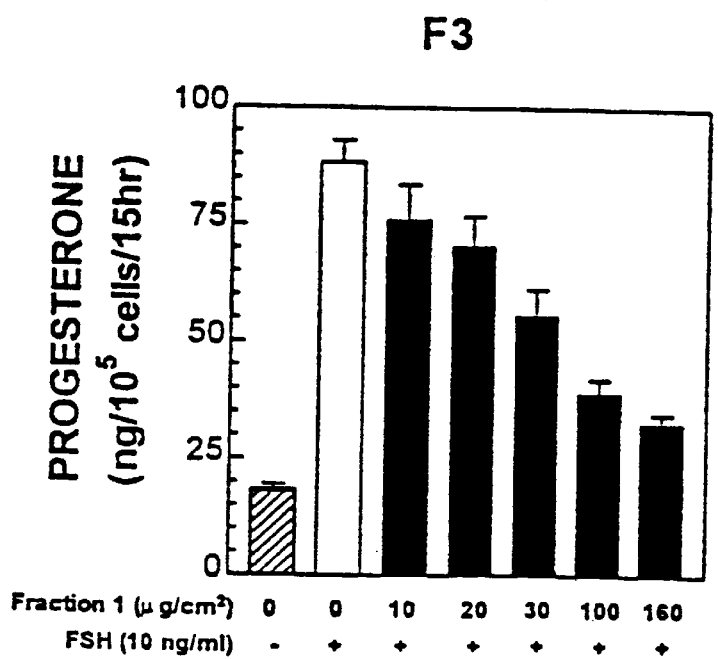
FIGS. 13A–13C Dose-response effect of solid form of fraction 1 of basal lamina on FSH-induced progesterone production. Granulosa cells from the third (F3), developing fifth, sixth and seventh (F5–7) largest preovulatory and immature (SYF) follicles were incubated in 96-well plate that were pre-coated with different amounts of fraction 1 of fluidized basal lamina. The cells were incubated for 15 hr in the presence and absence of FSH (10 ng/ml) and the progesterone content of the incubation medium was measured. Data are mean±SEM of nine incubations from three separate experiments.
Figure 13B:
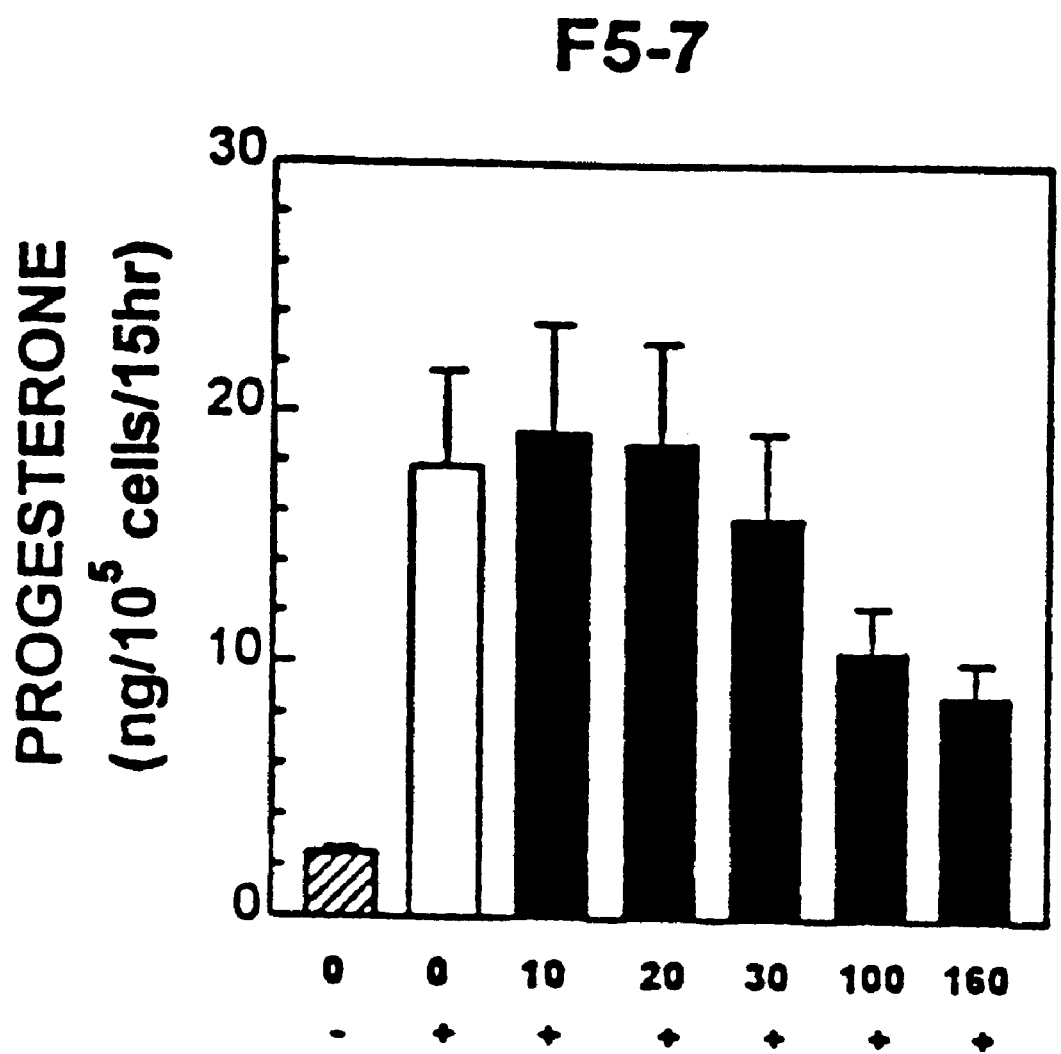
Figure 13C:
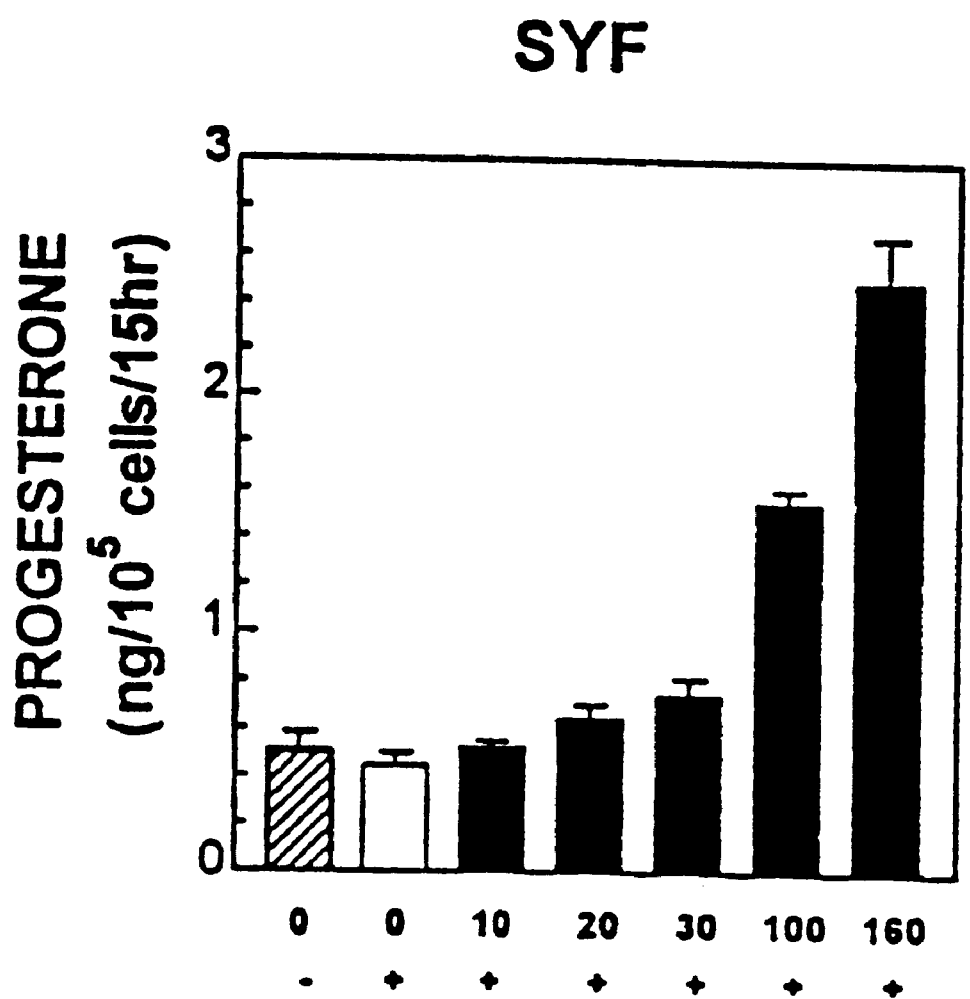
Figure 15A:
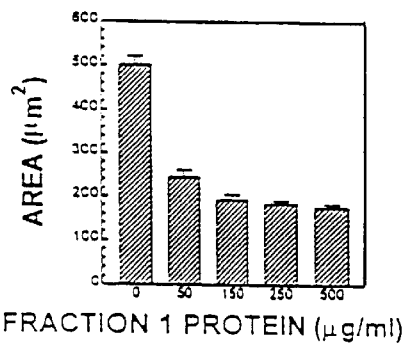
FIGS. 15A, 15D, 15G), developing (F3.
Figures 15B, 15C:
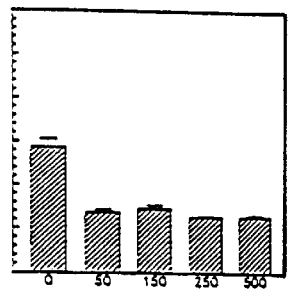
FIGS. 15B, 15E, 15H), immature (SYF.
FIGS. 15C, 15F, 15I) chicken ovarian follicles were incubated in serum free medium 199 for 15 hr in the absence or presence of fraction 1 protein (50–500 $\mu$g/ml) which was added as liquid. Each point is mean±SEM of 50 or more cells.
Figure 15D:
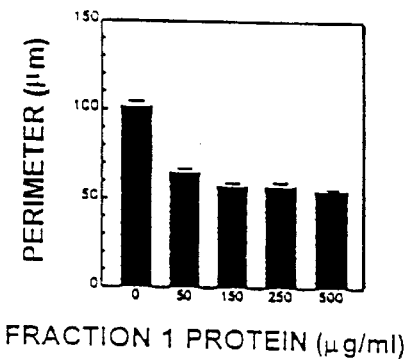
Figures 15E, 15F:
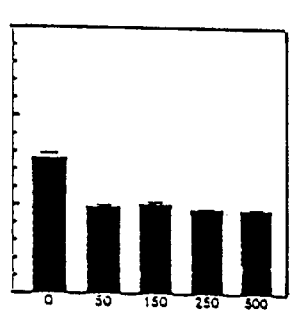
Figure 15G:
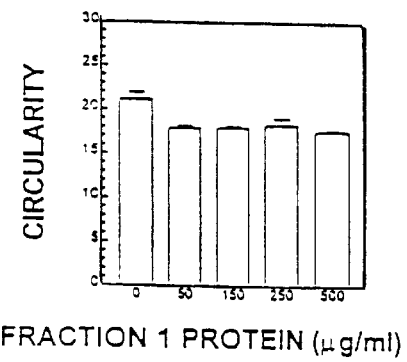
Figure 15H:
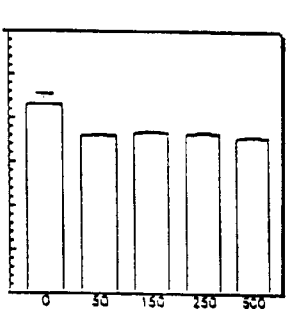
Figure 15I:
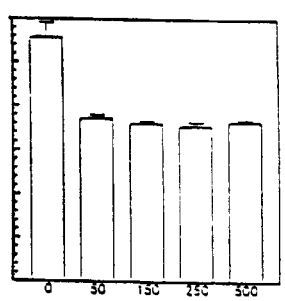

Effect of Solubilized Basal Lamina on FSH-induced Progesterone Production In Vitro The effects of solubilized basal lamina on follicle-stimulating hormone (FSH-) promoted progesterone production by granulosa cells were also assessed. Similar to observations made for LH, FSH-stimulated progesterone production by differentiating (F3) granulosa cells was attenuated in culture wells pre-coated with fraction 1 (FIG. 13A); by comparison, the stimulatory effects of FSH in undifferentiated (SYF) cells was enhanced by the solid form of fraction 1 (FIG. 13C). As observed for LH effect, FSH-induced progesterone production in wells that contained the highest concentration of solid form of fraction 1 remained higher than progesterone levels in control wells (FIG. 13A and 13B).

Figure 12A:
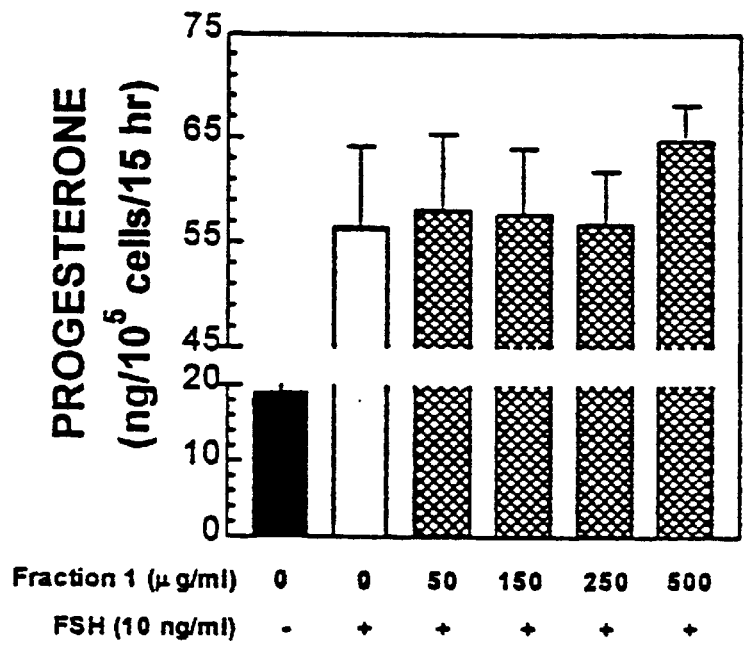
FIGS. 12A–12C Dose-response effect of liquid form of fraction 1 of basal lamina on FSH-induced progesterone production. Granulosa cells from the third (F3), developing fifth, sixth and seventh (F5–7) largest preovulatory and a pool of small yellow follicles (immature, SYF) were placed in 96-well plates and different amounts of fraction 1 were added as liquid. The mixture was incubated for 15 hr in the presence and absence of FSH (10 ng/ml) and the progesterone content of the incubation medium was measured. Data are mean±SEM of nine incubations from three separate experiments.
Figure 12B:
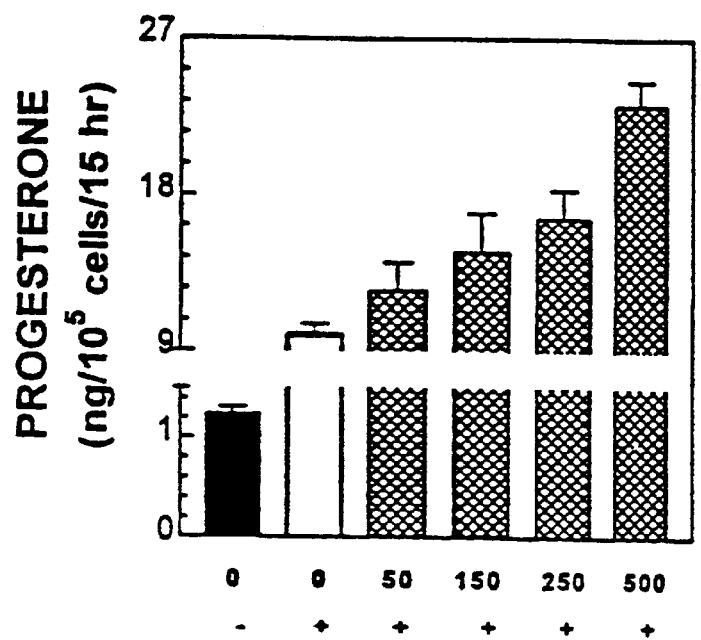
Figure 12C:
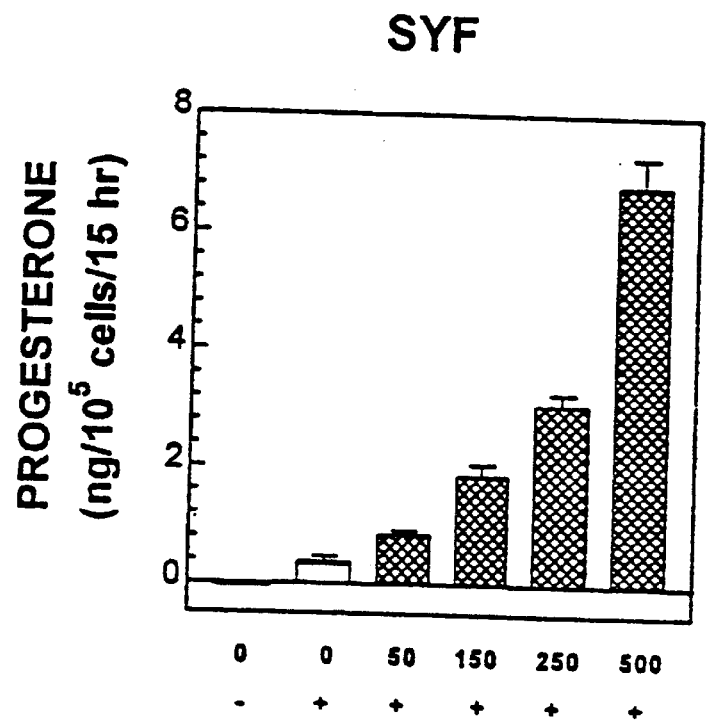

FSH also interacted with the liquid form of fraction 1 to regulate progesterone production by granulosa cells. In the liquid form, the solubilized basal lamina protein did not suppress the stimulatory action of FSH (FIG. 12). The stimulatory effect of FSH on progesterone production in both differentiating (F3, F5–7) or undifferentiated (SYF) granulosa cells was further enhanced by the liquid form of fraction 1 (FIG. 12). The effect of FSH on steroidogenesis on granulosa cells obtained from mature F1 follicles was not examined, because, it has been reported that FSH has little or no effect on these cells.

In summary, the basal lamina isolated from avian ovarian follicle has the ability to regulate granulosa cell function. The data support the view that basal lamina of avian ovarian follicle is biologically active because, alone, it is able to regulate steroid hormone synthesis in the absence of other known regulators of granulosa cell function. In addition it is noted that the effect of fraction 1 of solubilized basal lamina on steroidogenesis was influenced by the state of granulosa cell differentiation. Fraction 1 was more effective in stimulating steroidogenesis in undifferentiated granulosa cells isolated from immature follicles than in differentiated cells obtained from mature follicles. The exact loci of action of fraction 1 protein or their mechanisms of action are unknown. The effect of fraction 1 of solubilized basal lamina on progesterone production by granulosa cells was influenced by the form in which the matrix material was introduced into the culture system. When added as liquid to the incubation mixture fraction 1 of solubilized basal lamina enhanced progesterone production by chicken granulosa cells at all stages of differentiation. In contrast, when presented in solid form, fraction 1 alone increased progesterone production by less differentiated granulosa cells but suppressed it in differentiated ones.

In the present study, solubilized basal lamina interacted with pituitary-derived gonadotropic hormones to regulate chicken granulosa cell function. LH- or FSH-induced progesterone production by chicken granulosa cells was suppressed by fraction 1 of solubilized basal lamina regardless of the form of exposure to the cell. These data suggest that the basal lamina or its components interact with gonadotropic hormones to regulate granulosa cell function in vivo. Furthermore, the current data may be a reflection of the differential effects of basal lamina on granulosa cells in different states of differentiation during follicular development in vivo.

The present results demonstrate for the first time that basal lamina of the ovarian follicle is capable of regulating granulosa cell function. It has been reported that basement membrane deposited by bovine corneal endothelial cells caused rat and human granulosa cells to become more differentiated with increased steroidogenesis. The stimulatory effects of fraction 1 of basal lamina on progesterone production in undifferentiated cells may be due to differentiation caused by the matrix proteins.

Fraction 1 of fluidized basal lamina caused F1, F3, F5–7, and SYF granulosa cells to become rounded (FIGS. 14A–I and 15A–I); thus the effect of fluidized basal lamina on progesterone production in granulosa cells was accompanied with rounding of the cells. It was shown that extracellular matrix protein-induced increase in progesterone production by granulosa cells was accompanied by changes in cell shape. The relation between spherical shape and elevated progesterone production in granulosa cells has been reported. It was shown that rat or human granulosa cells grown in collagen gel matrix were rounded and produced greater amounts of progesterone than their counterparts that were spread on plastic culture surface.

In summary, pure and complete basal lamina was isolated from the largest preovulatory follicles of the chicken ovary and solubilized. The fluidized basal lamina, alone, regulated steroid hormone synthesis in granulosa cells. In addition, it modulated the stimulatory actions of LH or FSH on progesterone synthesis in chicken granulosa cells. These effects of fluidized basal lamina were influenced by the state of granulosa cell differentiation (stage of follicular development).

EXAMPLE 10

Effect of Solubilized FBM on Granulosa Cell Morphology In Vitro

Morphometric Analysis of Cells

Light microscopic images of granulosa cells were collected from at least five identical areas of each incubation well or coverslip on an inverted Nikon microscope (20× objective) and stored. The outlines of individual cells were traced using the following parameters: mean surface area covered by each cell, cell perimeter, and circularity were obtained with Optimas 6.0 Software (Bothell, Wash.). The higher that circularity (which is independent of size), the greater the irregularity of cell profile. A perfect circle has a circularity value of 12.

RESULTS

Effect of solubilized Basal Lamina on the Morphology of Granulosa cells

The morphometric parameters of differentiated (F1), differentiating (F3) and undifferentiated (SYF) granulosa cells incubated for 6 hr in wells containing dried fraction 1 of solubilized basal lamina are shown in FIG. 14. Dried fraction 1 reduced the mean area occupied by granulosa cells at all stages of differentiation (FIGS. 14A–C). Similarly, the perimeter of cells incubated in fraction 1 pre-coated wells was less than that of cells incubated on plastic (FIGS. 14D–F). Moreover, the cells incubated on plastic were more irregular than those incubated on fraction 1 (FIGS. 14G–I). As such, in wells pre-coated with fraction 1 of solubilized basal lamina, granulosa cells assumed a morphology that approximated the shape of chicken granulosa cells in vivo (in intact membrane granulosa). Granulosa cells incubated on dried fraction 1 formed clusters(data not shown) similar to what has been observed for intact basal lamina. To assess the influence of storage on the effect of solubilized basal lamina granulosa cell shape, fraction 1 was dried in wells and kept at 40° C. Granulosa cell incubated in fraction 1-containing wells that were stored at 40° C. for 12 or more months became rounded similar to observations made for granulosa cells incubated in freshly prepared fraction 1-containing dishes (results not shown).

The observation that granulosa cells that attached to plastic in close proximity to intact basal lamina were less flattened than cells in control wells suggested that basal lamina is a source of soluble morphogenic factor(s). Therefore, additional experiments were conducted to examine the effects of fraction 1 as liquid on cell shape. When added as liquid to the incubation mixture, the effect of fraction 1 fluidized basal lamina on granulosa cell shape was similar to that observed for cells incubated in wells that were pre-coated with the matrix material (results not shown).

FIG. 15 shows the morphometric parameters of granulosa cells incubated in wells to which fraction 1 was added as liquid. The mean area occupied by differentiated (F1), differentiating (F3) or undifferentiated (SYF), cells was less in wells to which fraction 1 was added (FIGS. 15A–C). Likewise, the perimeter (FIGS. 15D–F) and circularity (FIGS. 15G–I) of granulosa cells incubated in wells to which fraction 1 was added were less than those of control cells. It was noted that the cells were covered by fluidized basal lamina especially in the wells that contained 30 $\mu$g/ml or greater matrix material.

DISCUSSION

The ability of the basal lamina to influence cell shape was not affected by solubilization, as fraction 1 caused granulosa cells to become rounded. In addition it is noteworthy that, the storage of fluidized basal lamina (fraction 1) containing dishes at 4° C. for longer that twelve months had no apparent effect on its ability to cause shape changes in granulosa cells.

In summary, the structure of pure and intact basal lamina isolated from hen ovarian follicle is similar to that observed for basal lamina in the intact follicle. It influenced the shape of granulosa cells, the cells that it is in association with in vitro. Both the intact basal lamina and its fluidized form can be stored (preferably at 4° C. and in a dehydrated state) for 1–2 years without losing their ability to influence cell shape. One advantage of the utility of intact basal lamina is that it could provide data on in vivo behavior (responses); it can be used for the culture of cells in experiments designed to examine the influence of the basement membrane microenvironment on cell structure and function. For example, this natural basal lamina can be used to test in vitro, the potential of tumor cells to metastasize.

What is claimed is:

1. A composition comprising intact basement membrane of avian ovarian follicle tissue of a vertebrate, wherein the basement membrane is substantially free of cells of said vertebrate and the basement membrane is retained in its natural three dimensional shape.

2. The composition of claim 1 formed as a multi-layered construct comprising two or more sheets of said basement membrane.

3. The composition of claim 1 wherein the basement membrane comprises basal lamina delaminated from the granulosa cells of avian ovarian follicle tissue.

4. The composition of claim 1 for use in supporting the growth of eukaryotic cells, said composition further comprising
culture-ware covered with said basement membrane.

5. A composition comprising basement membrane of avian ovarian follicle tissue of a vertebrate, wherein the basement membrane is substantially free of cells of said vertebrate, and wherein the basement membrane is in a fluidized form.

6. The composition of claim 5 wherein said basement membrane is fluidized by treating the basement membrane with a chaotropic agent to solubilize the basement membrane.

7. The composition of claim 4 further comprising added nutrients to support the growth of said cells.

8. A composition for use in supporting the growth of eukaryotic cells comprising basement membrane of avian ovarian follicle tissue of a vertebrate, wherein the basement membrane is substantially free of cells of said vertebrate, and wherein the basement membrane is in a fluidized form said composition further comprising culture-ware covered with said fluidized basement membrane.

9. A method for supporting the growth and differentiation of eukaryotic cells in vitro, said method comprising the step of contacting the cells in vitro with a cell growth substrate comprising basement membrane of avian ovarian follicle tissue, under conditions conducive to the growth and proliferation of said cells, wherein the basement membrane comprises a basal lamina and wherein the basal lamina is delaminated from the granulosa cells of the avian ovarian follicle tissue.

10. The method of claim 9 wherein the step of contacting the cells with a cell growth substrate comprises culturing the cells on culture-ware that has been coated with fluidized basal lamina.

11. The method of claim 9, wherein the step of contacting the cells with a cell growth substrate comprises adding fluidized basal lamina to liquid cell culture media.

* * * * *